United States Patent
Forutanpour et al.

(10) Patent No.: US 9,071,679 B2
(45) Date of Patent: *Jun. 30, 2015

(54) CONTROLLING ACCESS TO A MOBILE DEVICE

(71) Applicant: QUALCOMM Incorporated, San Diego, CA (US)

(72) Inventors: Babak Forutanpour, San Diego, CA (US); Shyam K. Parekh, Carlsbad, CA (US); John Forrester, San Diego, CA (US); Harsha Rajendra Prasad, Glendale, CA (US)

(73) Assignee: Qualcomm Incorporated, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/265,942

(22) Filed: Apr. 30, 2014

(65) Prior Publication Data

US 2014/0235225 A1   Aug. 21, 2014

Related U.S. Application Data

(63) Continuation of application No. 13/440,317, filed on Apr. 5, 2012, now Pat. No. 8,750,852.

(60) Provisional application No. 61/552,396, filed on Oct. 27, 2011.

(51) Int. Cl.
*H04M 1/24* (2006.01)
*H04M 1/02* (2006.01)
(Continued)

(52) U.S. Cl.
CPC ............... *H04M 1/24* (2013.01); *G06F 21/32* (2013.01); *H04M 1/66* (2013.01);

(Continued)

(58) Field of Classification Search
CPC ..... G06F 3/044; G06F 3/03547; G06F 3/041; G06F 3/0488; G06F 3/0416; G06F 3/017; G06F 2203/04808
USPC ................ 455/414.1–414.4, 418–420, 550.1, 455/556.1–556.2, 566; 345/581, 594, 660, 345/156, 173–175
See application file for complete search history.

(56) References Cited

U.S. PATENT DOCUMENTS 5,243,645 A    9/1993   Bissell et al.
5,659,596 A    8/1997   Dunn
(Continued)

FOREIGN PATENT DOCUMENTS

CN    1629870 A    6/2005
CN    201383157 Y  1/2010
(Continued)

OTHER PUBLICATIONS

International Search Report—PCT/US2012/059593—ISA/EPO—Jun. 12, 2012.

*Primary Examiner* — Kashif Siddiqui
(74) *Attorney, Agent, or Firm* — Kilpatrick Townsend & Stockton LLP

(57) ABSTRACT

Various arrangements for customizing a configuration of a mobile device are presented. The mobile device may collect proximity data. The mobile device may determine that a user has gripped the mobile device based on the proximity data. A finger length of the user may be determined using the proximity data. Configuration of the mobile device may be customized at least partially based on the determined finger length of the user.

30 Claims, 12 Drawing Sheets

(51) Int. Cl.
  *G06F 21/32* (2013.01)
  *H04M 1/725* (2006.01)
  *A61B 5/107* (2006.01)
  *H04M 1/66* (2006.01)
  *A61B 5/00* (2006.01)

(52) U.S. Cl.
  CPC ..... *H04M 1/72577* (2013.01); *H04M 2250/12* (2013.01); *H04M 2250/22* (2013.01); *A61B 5/6898* (2013.01); *A61B 5/1072* (2013.01); *H04M 1/0279* (2013.01)

(56) References Cited

U.S. PATENT DOCUMENTS

| | | | |
|---|---|---|---|
| 5,974,162 | A | 10/1999 | Metz et al. |
| 6,125,176 | A | 9/2000 | Foladare et al. |
| 6,311,272 | B1 | 10/2001 | Gressel |
| 6,421,453 | B1 | 7/2002 | Kanevsky et al. |
| 6,429,927 | B1 | 8/2002 | Borza |
| 6,487,662 | B1 | 11/2002 | Kharon et al. |
| 7,130,452 | B2 | 10/2006 | Bolle et al. |
| 7,133,792 | B2 | 11/2006 | Murakami et al. |
| 7,764,274 | B2 * | 7/2010 | Westerman et al. .......... 345/173 |
| 7,828,739 | B2 | 11/2010 | Arnold |
| 7,953,462 | B2 | 5/2011 | Vartanian et al. |
| 8,031,175 | B2 | 10/2011 | Rigazio et al. |
| 8,334,993 | B2 | 12/2012 | Singh |
| 2001/0048025 | A1 | 12/2001 | Shinn |
| 2005/0030151 | A1 | 2/2005 | Singh |
| 2005/0068166 | A1 | 3/2005 | Baker |
| 2006/0034726 | A1 | 2/2006 | Sunshine et al. |
| 2006/0195328 | A1 | 8/2006 | Abraham et al. |
| 2006/0206724 | A1 | 9/2006 | Schaufele et al. |
| 2007/0055666 | A1 | 3/2007 | Newbould et al. |
| 2007/0198937 | A1 | 8/2007 | Paris |
| 2007/0214228 | A1 | 9/2007 | Horvitz et al. |
| 2007/0264981 | A1 | 11/2007 | Miller |
| 2008/0025842 | A1 | 1/2008 | Marini et al. |
| 2008/0092245 | A1 | 4/2008 | Alward et al. |
| 2008/0292079 | A1 | 11/2008 | Toutain et al. |
| 2009/0006613 | A1 | 1/2009 | Toutain et al. |
| 2009/0318815 | A1 | 12/2009 | Barnes et al. |
| 2009/0326383 | A1 | 12/2009 | Barnes et al. |
| 2010/0042564 | A1 | 2/2010 | Harrison et al. |
| 2010/0134424 | A1 * | 6/2010 | Brisebois et al. ............. 345/173 |
| 2010/0225443 | A1 | 9/2010 | Bayram et al. |
| 2010/0248822 | A1 | 9/2010 | Migos et al. |
| 2011/0115604 | A1 | 5/2011 | Sobel et al. |
| 2011/0254865 | A1 * | 10/2011 | Yee et al. ...................... 345/661 |
| 2012/0002563 | A1 | 1/2012 | Flanagan |
| 2012/0036261 | A1 | 2/2012 | Salazar et al. |
| 2013/0109369 | A1 | 5/2013 | Forutanpour et al. |

FOREIGN PATENT DOCUMENTS

| | | |
|---|---|---|
| CN | 101782805 A | 7/2010 |
| JP | H05260188 A | 10/1993 |
| JP | 2001156921 A | 6/2001 |
| JP | 2003163739 A | 6/2003 |
| JP | 2007116602 A | 5/2007 |
| JP | 2011523730 A | 8/2011 |
| WO | WO-2007113516 A1 | 10/2007 |
| WO | WO-2009131987 A2 | 10/2009 |
| WO | WO-2012091574 A1 | 7/2012 |

* cited by examiner

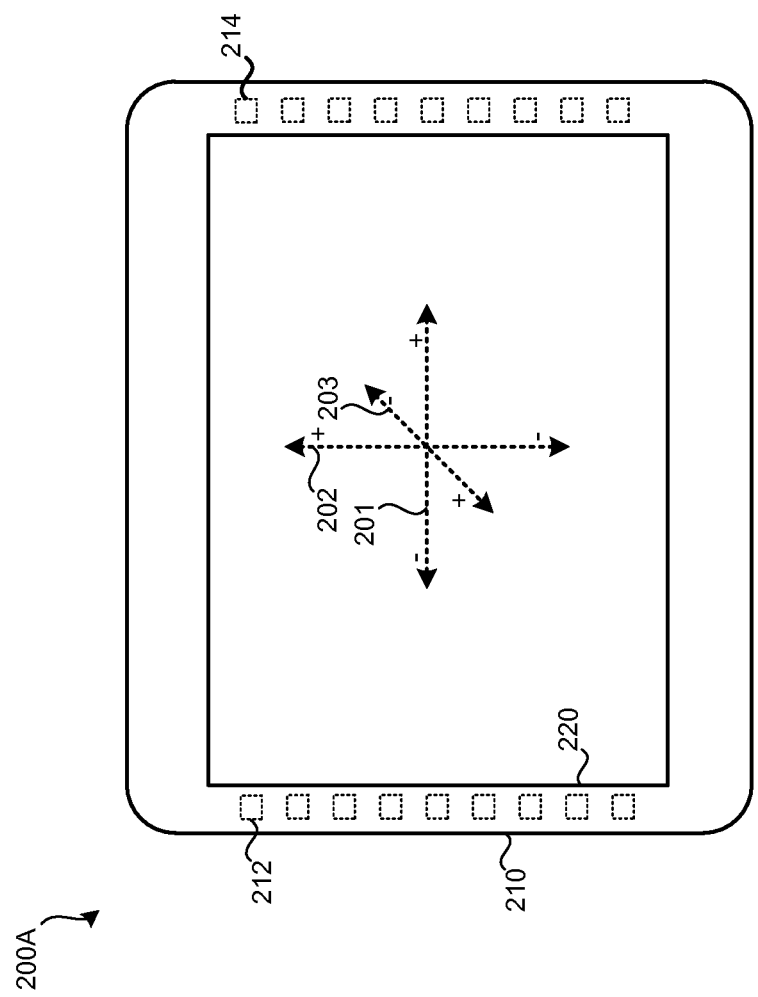

CONTROLLING ACCESS TO A MOBILE DEVICE

CROSS REFERENCES

This application is a continuation of U.S. patent application Ser. No. 13/440,317, filed Apr. 5, 2012, which claims priority to Provisional Application No. 61/552,396 filed on Oct. 27, 2011, entitled "Controlling Access to a Mobile Device Using Hand Size." These Applications are hereby incorporated by reference for all purposes. U.S. patent application Ser. No. 12/851,413, entitled "Communication Management Utilizing Destination Device User Presence Probability," filed Aug. 5, 2010, is hereby incorporated by reference for all purposes.

BACKGROUND

Multiple users may interact with the same mobile device, such as the same tablet computer or gaming device. For example, a family having a child, father, and mother may have a single tablet computer, which each family member uses. Each of these users may interact with the mobile device in a different way: the applications used by the father may be different from the applications typically used by the child. Further, use restrictions, such as on the child, may be desired to be imposed to prevent the child from accessing inappropriate content.

In order to customize a configuration of a mobile device for a particular user, each user may be required to log in to the mobile device before the mobile device is available for use. A login process, such as providing a username and password, may be time-consuming and/or beyond the ability of certain users (for example, a young child may not be able to remember and/or input a password). Further, passwords may be forgotten, stolen, or guessed. Accurately identifying a user without such a login process may more efficiently and/or effectively control access to a mobile device.

SUMMARY

In some embodiments, a method for customizing a configuration of a mobile device is presented. The method may include collecting, by the mobile device, proximity data. The method may include determining, by the mobile device, that a user has gripped the mobile device based on the proximity data. The method may include determining, by the mobile device, a finger length of the user using the proximity data. The method may include customizing, by the mobile device, the configuration of the mobile device at least partially based on the finger length of the user.

Embodiments of such a method may include one or more of the following: The method may include customizing, by the mobile device, the configuration of the mobile device comprises limiting a data transmission rate of the mobile device. The method may include receiving, by the mobile device, a text message routed to the mobile device at least partially based on the user gripping the mobile device, wherein a mobile phone linked with the user does not ring or vibrate in response to the text message. The method may include using the proximity data, determining, by the mobile device, that the user has gripped the mobile device with two hands. Determining, by the mobile device, the finger length of the user using the proximity data may comprise determining, by the mobile device, a first finger length of a left hand of the user and a second finger length of a right hand of the user. The mobile device may comprise a housing. The housing may have a front surface and a rear surface. The front surface may comprise a display. The proximity data may be collected by the mobile device using a plurality of proximity sensors arranged on the rear surface of the housing of the mobile device. The mobile device may be configured to measure a first finger length of the user on a first hand and a second finger length of a second hand when the first hand of the user grips a first side of the mobile device and the second hand of the user grips a second side of the mobile device. The first hand of the user and the second hand of the user may simultaneously grip the mobile device. Customizing, by the mobile device, the configuration of the mobile device may comprise selecting functions from a set of functions available to the user at least partially based on the finger length of the user. The method may include receiving, by the mobile device, proximity data for each user of a plurality of users. The plurality of users may comprise the user. The proximity data may correspond to each user is used to determine the finger length for each user of the plurality of users. The method may include storing, by the mobile device, a user profile for each user, wherein the user profile identifies the finger length for the corresponding user.

In some embodiments, a mobile device may be configured to customize a configuration. The mobile device may include a housing. The mobile device may include a front surface comprising a display. The mobile device may include a rear surface. The mobile device may include two pairs of capacitive proximity sensors. The capacitive proximity sensors may be configured to collect proximity data that indicates proximity to a triggering entity. The mobile device may include a processor. The mobile device may include a memory communicatively coupled with and readable by the processor and having stored therein processor-readable instructions. The processor-readable instructions, when executed by the processor, may cause the processor to: determine that a user has gripped the mobile device based on the proximity data; determine a finger length of the user using the proximity data; and customize the configuration of the mobile device at least partially based on the finger length of the user.

Embodiments of such a mobile device may include one or more of the following: The mobile device may include a transmitter, wherein a data transmission rate of the transmitter is adjusted at least partially based on the configuration of the mobile device customized The processor-readable instructions may further comprise processor-readable instructions configured to cause the processor to present a text message routed to the mobile device at least partially based on the user gripping the mobile device, wherein a mobile phone linked with the user does not ring or vibrate in response to the text message. The processor-readable instructions may further comprise processor-readable instructions configured to cause the processor to, using the proximity data, determine that the user has gripped the mobile device with two hands. The processor-readable instructions configured to cause to the processor to determine the finger length of the user using the proximity data may comprise processor-readable instructions configured to cause the processor to determine a first finger length of a left hand of the user and a second finger length of a right hand of the user. The two pairs of capacitive proximity sensors may be arranged on the rear surface of the housing of the mobile device. The processor-readable instructions configured to cause the processor to customize the configuration of the mobile device may comprise processor-readable instructions configured to cause the processor to select functions from a set of functions available to the user at least partially based on the finger length of the user. The processor-readable instructions may further comprise processor-readable instructions configured to cause the processor to receive proximity data for each user of a plurality of users. The plurality of users comprises the user. The proximity data corresponding to each user may be used to determine the finger length for each user of the plurality of users. The processor-readable instructions may further comprise processor-readable instructions configured to cause the processor to cause a user profile for each user to be stored, wherein the user profile identifies the finger length for the corresponding user.

In some embodiments, a computer program product residing on a non-transitory processor-readable medium for customizing a configuration of a mobile device is presented. The computer program product may comprise processor-readable instructions configured to cause a processor to collect proximity data. The processor-readable instructions may be further configured to cause the processor to determine that a user has gripped the mobile device based on the proximity data. The processor-readable instructions may be further configured to cause the processor to determine a finger length of the user using the proximity data. The processor-readable instructions may be further configured to cause the processor to customize the configuration of the mobile device at least partially based on the finger length of the user.

The computer program product may include one or more of the following: The processor-readable instructions configured to cause the processor to customize the configuration of the mobile device may further comprise processor-readable instructions configured to cause the processor to limit a data transmission rate of the mobile device. The computer program product may further comprise processor-readable instructions configured to cause the processor to cause a text message routed to the mobile device at least partially based on the user gripping the mobile device to be presented, wherein a mobile phone linked with the user does not ring or vibrate in response to the text message. The computer program product may further comprise processor-readable instructions configured to cause the processor to, using the proximity data, determine that the user has gripped the mobile device with two hands. The processor-readable instructions configured to cause the processor to determine the finger length of the user using the proximity data may further comprise processor-readable instructions configured to cause the processor to determine a first finger length of a left hand of the user and a second finger length of a right hand of the user. The processor-readable instructions configured to cause the processor to customize the configuration of the mobile device may further comprise processor-readable instructions to cause the processor to select functions from a set of functions available to the user at least partially based on the finger length of the user. The computer program product may further comprise processor-readable instructions configured to cause the processor to receive proximity data for each user of a plurality of users. The plurality of users may comprise the user. The proximity data corresponding to each user is used to determine the finger length for each user of the plurality of users. The computer program product may further comprise processor-readable instructions configured to cause the processor to cause a user profile for each user to be stored, wherein the user profile identifies the finger length for the corresponding user.

In some embodiments, an apparatus for customizing a configuration of a mobile device may be presented. The apparatus may include means for collecting proximity data. The apparatus may include means for determining that a user has gripped the mobile device based on the proximity data. The apparatus may include means for determining a finger length of the user using the proximity data. The apparatus may include means for customizing the configuration of the mobile device at least partially based on the finger length of the user.

Embodiments of such an apparatus may include one or more of the following: The means for customizing the configuration of the mobile device may comprise means for limiting a data transmission rate of the mobile device. The apparatus may include means for presenting a text message routed to the mobile device at least partially based on the user gripping the mobile device, wherein a mobile phone linked with the user does not ring or vibrate in response to the text message. The apparatus may include means for determining, using the proximity data, that the user has gripped the mobile device with two hands. The means for determining the finger length of the user using the proximity data may comprise means for determining a first finger length of a left hand of the user and a second finger length of a right hand of the user. The means for collecting the proximity data may be arranged on a rear surface of the mobile device. The means for customizing the configuration of the mobile device may comprise means for selecting functions from a set of functions available to the user at least partially based on the finger length of the user. The apparatus may include means for receiving proximity data for each user of a plurality of users. The plurality of users may comprise the user. The proximity data corresponding to each user may be used to determine the finger length for each user of the plurality of users. The apparatus may include means for storing a user profile for each user, wherein the user profile identifies the finger length for the corresponding user.

BRIEF DESCRIPTION OF THE DRAWINGS

A further understanding of the nature and advantages of various embodiments may be realized by reference to the following figures. In the appended figures, similar components or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

FIG. 2A illustrates an embodiment of a mobile device configured for customizing a configuration of a mobile device using hand size.

Figure 5:
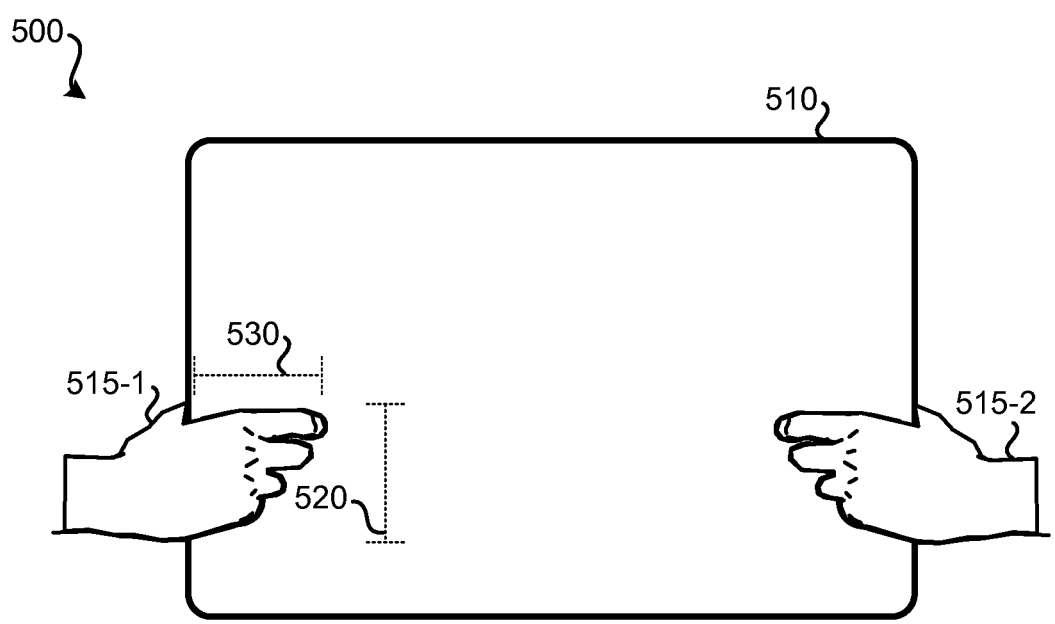

FIG. 5 illustrates another embodiment of a mobile device configured to customize a configuration based on hand size and/or finger length of the user gripping the mobile device being gripped by a user with small hands.

Figure 6:
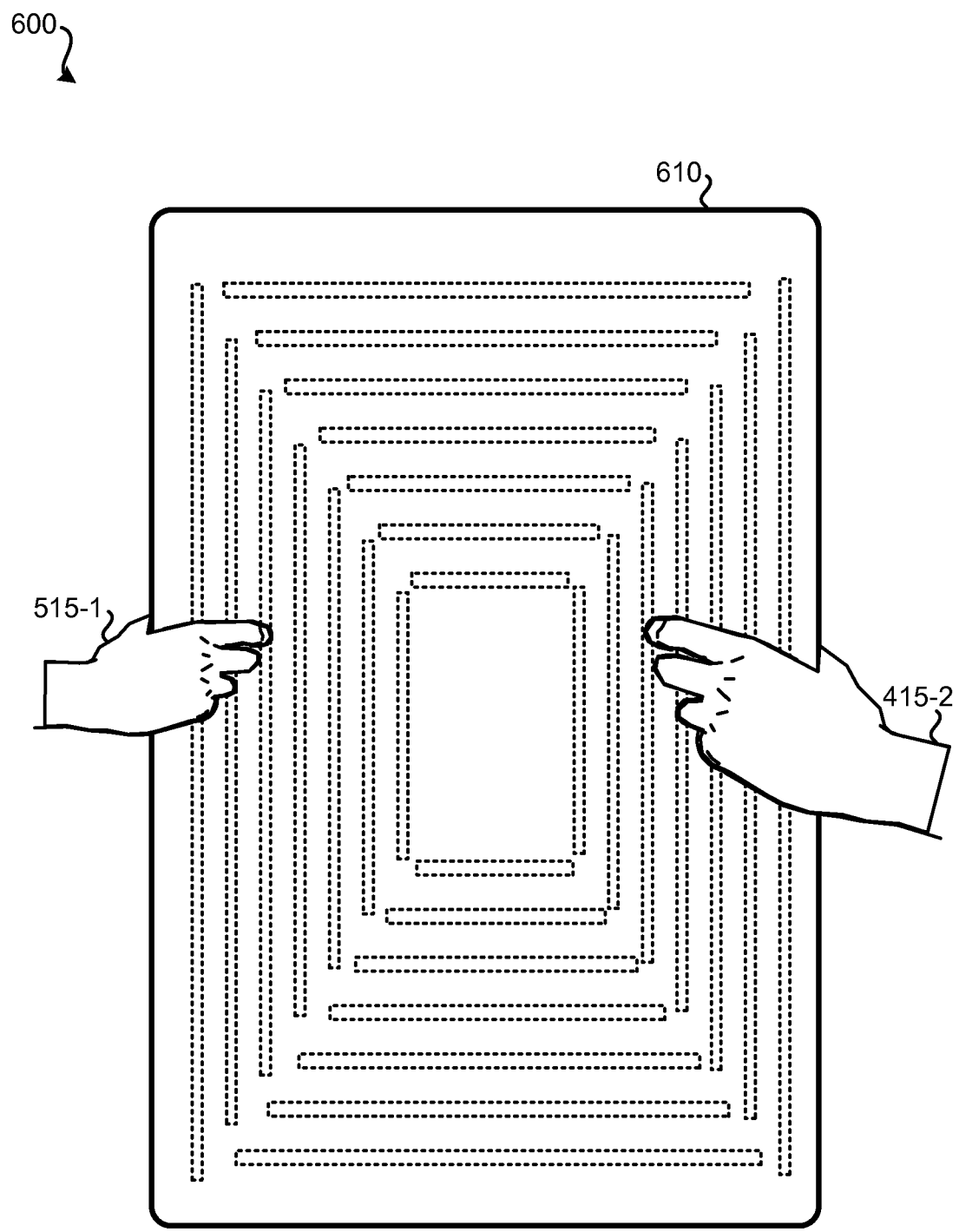

FIG. 6 illustrates an embodiment of a mobile device configured to customize a configuration based on finger length being gripped by hands of different sizes.

Figure 7:
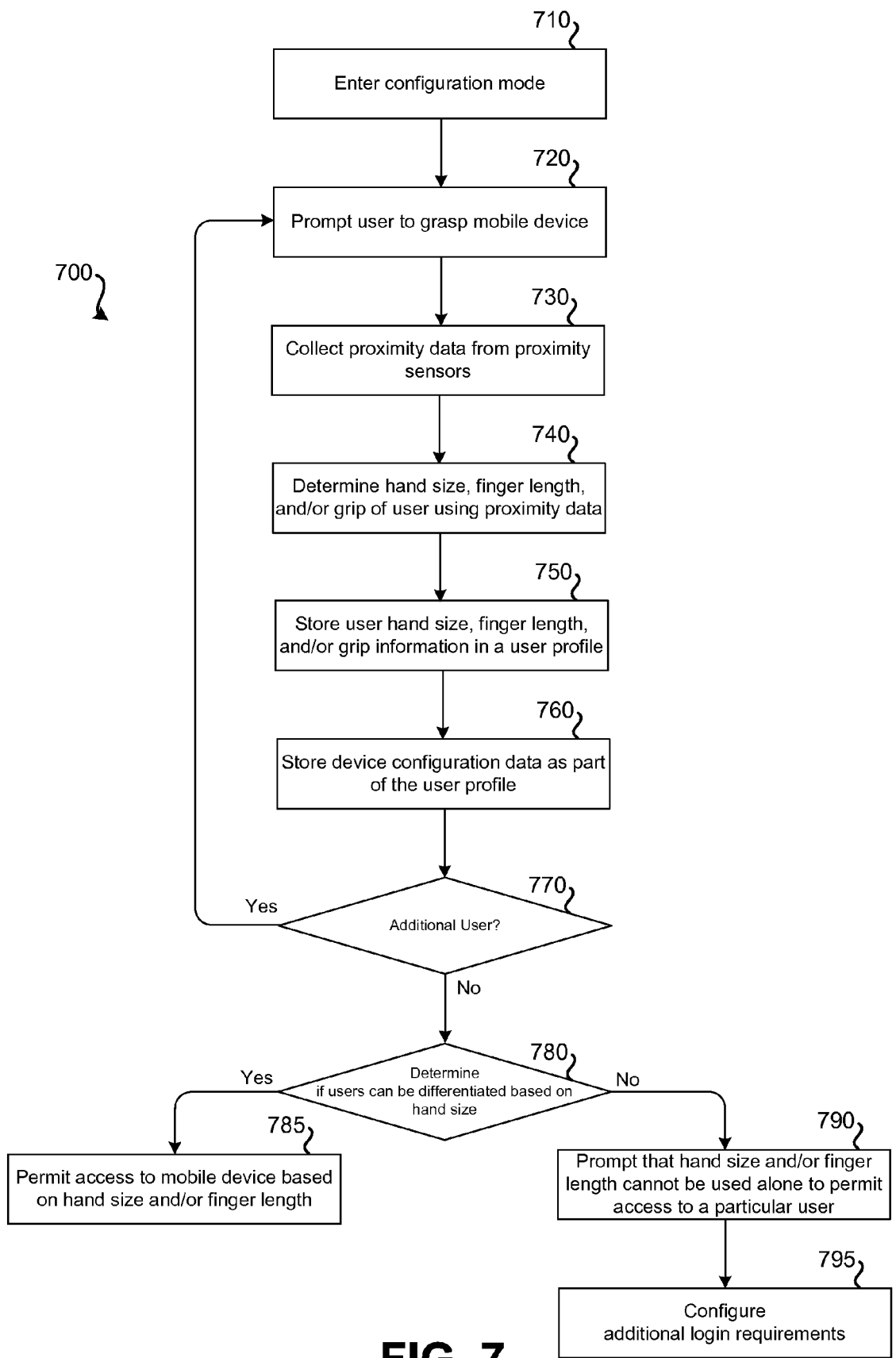

FIG. 7 illustrates an embodiment of a method for configuring a system that customizes a configuration based on hand size and/or finger length.

Figure 8:
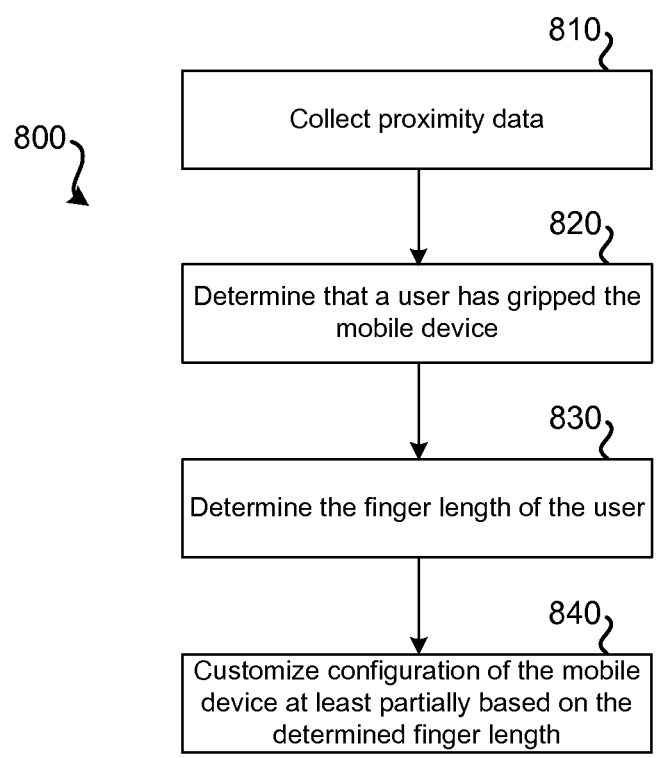

FIG. 8 illustrates an embodiment of a method for customizing a configuration of mobile device based on hand size and/or finger length of a user.

Figure 9:
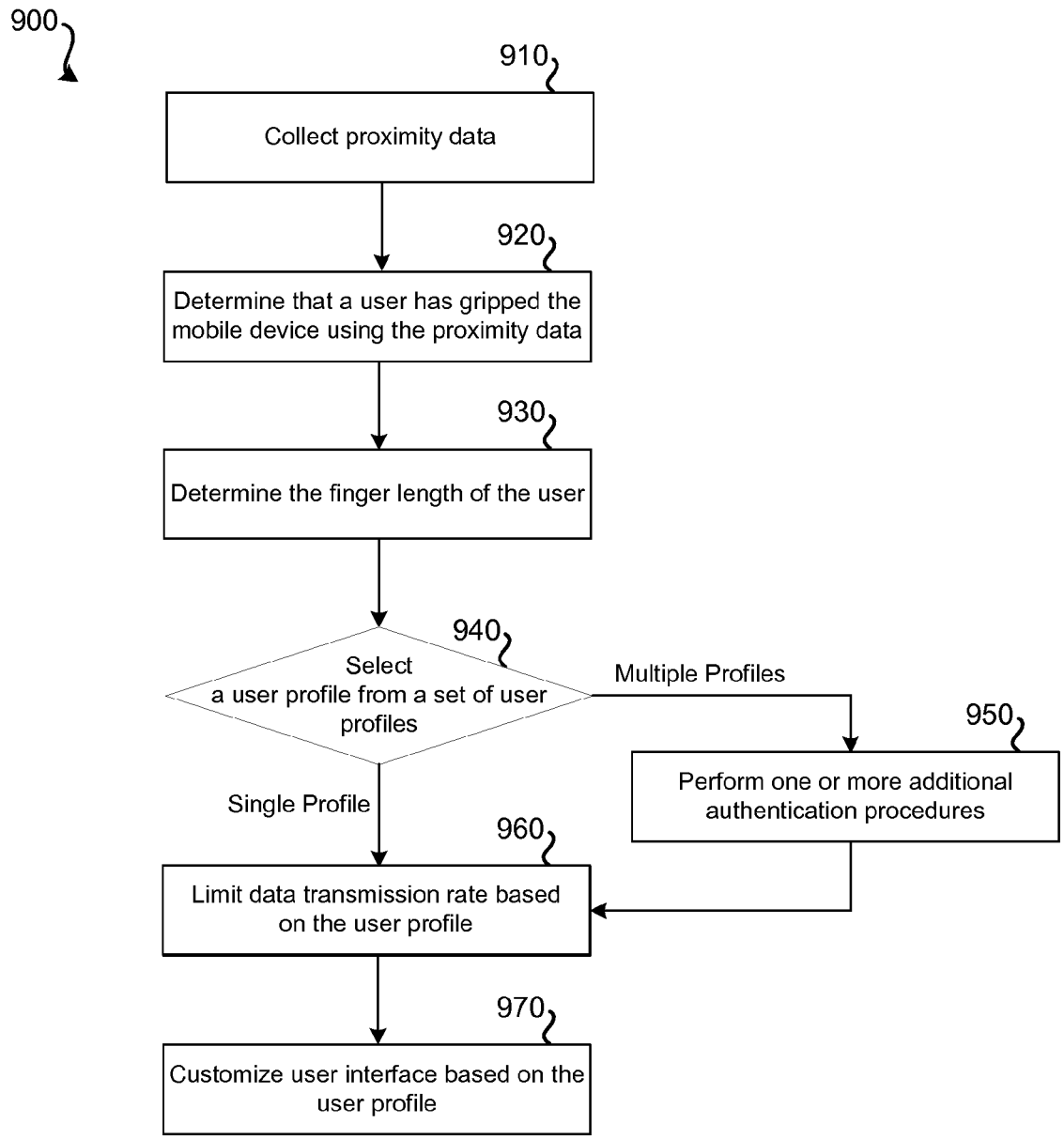

FIG. 9 illustrates another embodiment of a method for customizing a configuration of mobile device based on hand size and/or finger length of a user.

Figure 10:
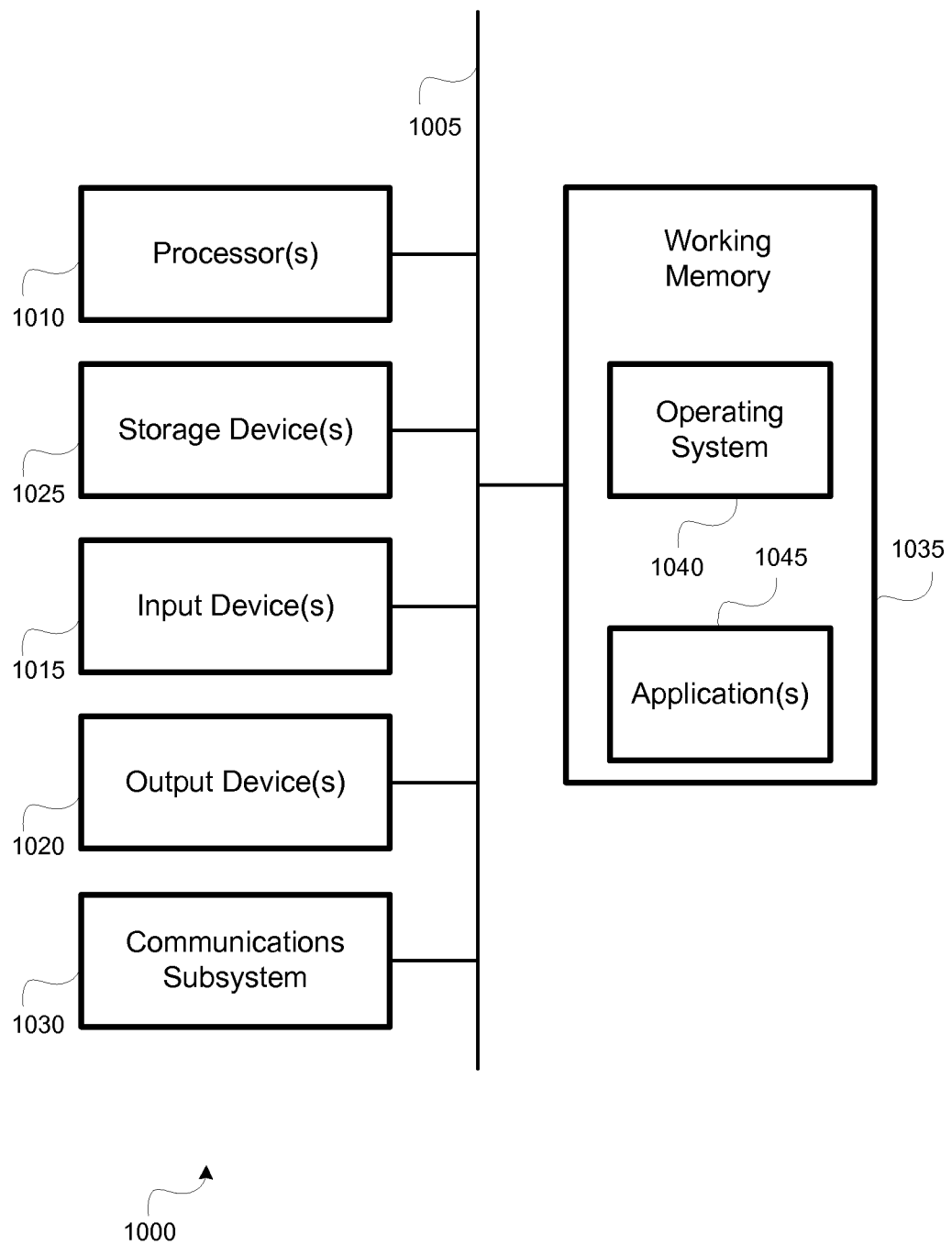

FIG. 10 illustrates an embodiment of a computer system.

DETAILED DESCRIPTION

Hand size and/or finger length may be used to determine how configuration of a mobile device (e.g., tablet computer, gaming device) is to be customized for use by a particular user. When a user grasps the mobile device, proximity data gathered using proximity sensors may be used to determine the size of the user's hand (e.g., hand width) and/or how long are one or more of the user's fingers. The user may be required to grip the mobile device with both hands on opposite sides of the mobile device. Such a grip involving both hands may prevent a user from forging a larger hand by using two hands together to imitate a single hand. This may be especially useful to prevent a child from forging a larger, adult hand that may be authorized for less restrictive access to the mobile device.

The configuration of the mobile device may be customized for a user in multiple ways. In some embodiments, which functions (e.g., applications) are available and/or the ordering of functions on a display to a user may be customized In some embodiments, customizing the configuration of the mobile device may involve decreasing or limiting the data rate of data being transmitted by the mobile device.

To determine a user's hand size and/or finger length, multiple proximity sensors may be used. Proximity sensors can be used to detect when a triggering entity, such as portion of a human body (e.g., a hand, a finger) is either 1) in contact with a proximity sensor or 2) near the proximity sensor. One type of proximity sensor is a capacitive proximity sensor that detects changes in capacitance. Such a capacitive proximity sensor may include one or two electrodes. A dual-electrode capacitive proximity sensor may detect the presence of a portion of a human body by measuring changes in capacitance between the two electrodes. Use of a capacitive proximity sensor may have the advantage of being more likely to be triggered by a human grip which completes the circuit than by conductive objects, such as coins or keys. Further, because capacitive proximity sensors can be triggered if a portion of a human body is near but not touching the capacitive proximity sensor, that portion of the human body may trigger the capacitive proximity sensor through thin materials such as cloth (e.g., pants, gloves) and mobile device cases.

Proximity sensors, which may be capacitive proximity sensors, may be arranged on a mobile device, such as a tablet computer, a cellular phone, or other mobile device, to detect the size of a user's hand or hands. To do this, multiple sets of dual-electrode capacitive proximity sensors can be used. In some embodiments, multiple single-electrode capacitive proximity sensors are used. Electrodes for capacitive proximity sensors may be arranged on opposite sides of a mobile device to detect touch in regions of the tablet computer typically held by a user.

Using such proximity sensors, a size of a user's hands may be identified. Using the size of the user's hands, it may be determined who a particular user is. For example, a training session may be conducted during which each user who may use the mobile device holds the device. The mobile device may then associate the detected hand size and/or finger length with the user. For example, in a family, a father may have the largest hands, followed by the mother, with a young child having the smallest hands. Determining a "size" of a hand may refer to determining a hand width. Determining a size of a hand may also include measuring an amount of flesh of a hand in contact with or near one or more proximity sensors. Two hands that are the same width may yield different measurements due to different compositions of muscle, bone, and skin. Determining finger length may involve measuring a distance of one or more of the user's fingers using proximity data collected by proximity sensors.

When one of the users handles the mobile device, operation of the mobile device may be customized for the user. This customization may not require any additional input from the user besides gripping the mobile device, possibly with two hands. In some embodiments, the listing of functions may be customized for each user: only functions approved for the child may be displayed if the child's hand size and/or finger length is detected. For the mother, all applications may be displayed, but with the mother's most used applications being listed first or in an order predefined by her.

Further, it may be desirable to limit a child's use of such a mobile device. For example, parents may not want a child to play with a mobile device all day (such as, at the expense of playing with schoolmates outside). Based on detection of the child's hand size and/or finger length, the child's user experience with the mobile device may be degraded. For example, the mobile device may transmit and/or receive wireless or cellular data at a reduced rate and/or at a reduced power level. In some embodiments, to limit the data transmission rate, the power level of the transmitter may be limited, and vice versa. Such a degrading of the child's user experience may result in the child being more likely to participate in other activities (e.g., due to boredom or frustration). In some embodiments, a hard cap on use may be imposed. For example, after 100 megabytes of data transmission and/or reception, the mobile device may be locked to prevent further use by the child based on his or her hand size for a time period, such as a day. Certain content, such as applications or websites, may also be prevented from being accessed by a user, such as the child, based on hand size and/or finger length.

In some embodiments, rather than a hand size being linked with a particular user, the hand size may be used to make a generalization about the user. For example, whenever hand size and/or finger length is determined to be below a certain threshold size and/or length, it may be assumed the user is a child and the user experience may be degraded by decreasing data transmission rates and/or access to certain functions of the mobile device. Therefore, a user profile may be established for a particular class of users, such as children. In addition to hand size and finger length, how a user grips the mobile device may affect the configuration of the mobile device. For example, different users may typically grip the same device in different locations or ways. Such differences may be detected and may be used to identify the user.

Figure 1:
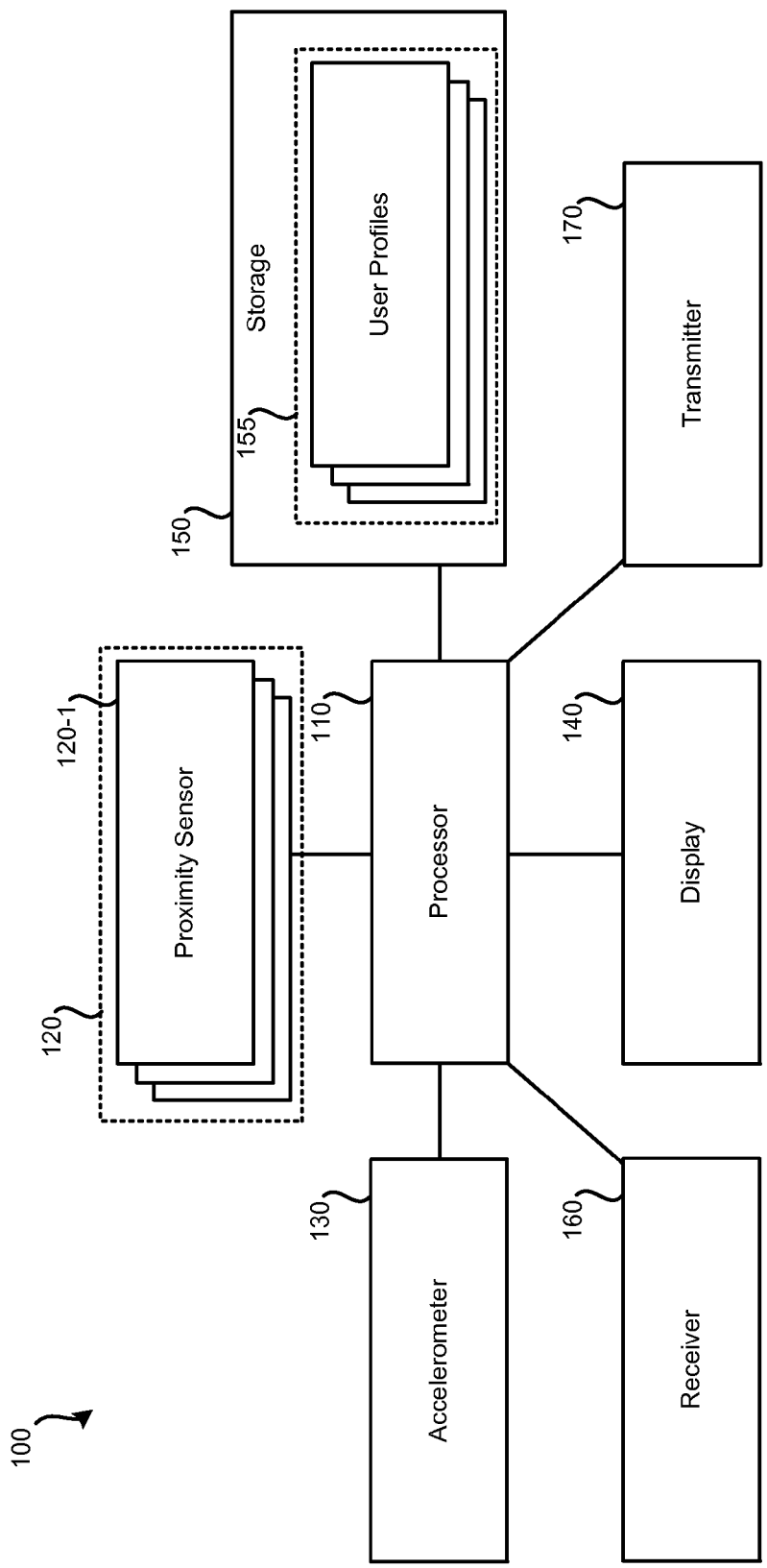
FIG. 1 illustrates a block diagram of an embodiment of a system configured for customizing a configuration of a mobile device using hand size and/or finger length.

FIG. 1 illustrates a block diagram of an embodiment of a system 100 configured for customizing a configuration of a mobile device using hand size and/or finger length. System 100 may include: processor 110, proximity sensors 120, accelerometer 130, display 140, storage 150, receiver 160, and transmitter 170. System 100 may be part of a larger system. For example, system 100 may be part of a mobile device that contains additional components. For example, the mobile device that system 100 may be a part of may be a cellular phone (e.g., a smartphone), a tablet computer, a personal digital assistant, or gaming device, to name only a few examples. System 100 may be part of a computer system, such as computer system 1000 of FIG. 10.

Processor 110 may be a general purpose or specialized processor configured to receive and process data from one or more components, such as proximity sensors 120, accelerometer 130, and receiver 160. Processor 110 may also interact with storage 150 and display 140, and provide data to transmitter 170 for transmission.

Processor 110 may be in communication with proximity sensors 120. System 100 may include one or more proximity sensors 120. As such, some embodiments may have two, three, four, or more proximity sensors in communication with processor 110. Each proximity sensor, such as proximity sensor, 120-1, may include a single-electrode capacitive proximity sensor. In some embodiments, one or more of the proximity sensors may be dual-electrode capacitive proximity sensors. As such, each proximity sensor, such as proximity sensor 120-1, may include one or two electrodes. Each of these proximity sensors may provide data to processor 110 that indicates whether a triggering entity is within range of the proximity sensor. Each proximity sensor may also transmit a magnitude value that indicates how close a triggering entity is to the electrode(s) of the proximity sensor. The triggering entity may be any entity that causes the capacitance measured by the proximity sensor to vary. When being used by a user, part of the user's body may serve as the triggering entity. A user's hand and/or fingers positioned near a proximity sensor may be sensed as the triggering entity by the proximity sensor. Such proximity sensors may be configured to determine when a triggering entity is in contact with the proximity sensor and when a triggering entity is close to the proximity sensor (collectively referred to as proximate). As such, for each proximity sensor of proximity sensors 120 to detect the presence of a triggering entity, the triggering entity does not need to be in direct contact with one or more electrodes of the proximity sensor.

While the above description of proximity sensors focuses on the use of capacitive proximity sensors, it should be understood that in some embodiments proximity sensors other than capacitive proximity sensors may be used. Further, some embodiments may use multiple types of proximity sensors; for example, a mobile device may contain both single-electrode and dual-electrode capacitive proximity sensors and/or other types of proximity sensors.

Processor 110 may be in communication with one or more accelerometers, such as accelerometer 130. Accelerometer 130 may provide acceleration data to processor 110. Such acceleration data may indicate a direction of acceleration and a magnitude of acceleration. For example, an angle to the ground at which system 100 is positioned (e.g., being held) may be determined using accelerometer 130 to sense the direction of gravity's pull. In some embodiments, more accurate results may be achieved by receiving acceleration data from multiple accelerometers. Such data may be averaged or otherwise combined by processor 110. Accelerometer 130 may be disabled when acceleration data is not needed, thus conserving power.

Processor 110 may be in communication with display 140. Display 140 may be used to visually present text and/or graphics to a user of a mobile device. Whether display 140 is active or inactive (e.g., turned on or off) may be at least partially based on data received from proximity sensors 120. For example, display 140 may be activated when proximity data from proximity sensors 120 indicate that the mobile device containing system 100 is being held by the user. As such, power consumed by display 140 may be decreased by decreasing the amount of time that display 140 is activated.

When a user's hand size and/or finger length is determined, display 140 may provide an indication of the user or class of users identified based on the determined hand size and/or the finger length.

Turning the display and/or other components of the mobile device on and/or off may also be at least partially based on input received from a user input device separate from the proximity sensors of the mobile device, such as a button. For instance, a user may press the button to indicate that the mobile device is be turned off Data from proximity sensors 120 may not be used to turn the mobile device on again until the mobile device has stopped being gripped (possibly for a threshold period of time). Therefore, if the user pushes the button, the mobile device does not turn back on if the user is still gripping the mobile device. If the user grips the mobile device after the mobile device has not been gripped for a period of time, the mobile device may turn on. In some embodiments, it may be desirable to turn on at least partially based on proximity data, but not to turn off based on proximity data. For example, if a user repositions his hands, it may be undesirable for the mobile device to inadvertently turn off Processor 110 may be able to read data from and write data to storage 150. Storage 150 may be a non-transitory storage medium used to store data related to user profiles that correspond to a particular user or a class of users. User profiles 155 may contain one or more user profiles. Each user profile may be associated with a specific user. For example, if a family uses a mobile device containing system 100, a user profile may be present for each of a father, a mother, and a child. More or fewer user profiles 155 may also be present. Each user profile of user profiles 155 may define various customizations, such as: a user identifier, hand size, finger length, grip properties (e.g., where and how the user typically grasps the mobile device), user interface preferences (e.g., order in which applications are presented, a listing of favorites), whether additional login data is required, device controls (e.g., data transmission rate limitations, power limitations, time usage limitations (e.g., total amount of time that the mobile device may be used by a user per unit of time, such as a day or hours of the day, during which use is prohibited), a (transmit and/or receive) data cap, parental restrictions (e.g., prevent a child from accessing inappropriate applications and/or websites). The user profiles may be created or modified during a configuration process in which the hand size and/or finger length of multiple users is determined and stored. A master user (e.g., an administrator, which may be a parent in a family) may define the various properties of each user profile, such as controls on a child's use of the mobile device.

In some embodiments, in addition to, or instead of, having user profiles for specific users, one or more user profiles 155 may be defined for classes of users. Age groups may be able to be estimated based on hand size and/or finger length. For example, young children typically have the smallest hands and shortest fingers. As they age, their hands may grow until approximately adulthood. As such, by determining the hand size of the user, at least an approximate age of the user may be estimated. For example, these estimates may be used to group users into one of three categories: young child, child, or adult. Each of these user classes may be associated with a user profile that defines characteristics as discussed in the previous paragraph. In some embodiments, if a hand size and/or finger length does not match a user profile associated with a particular user, a user profile for a class of users that corresponds to the user's hand size and/or finger length may be used.

Processor 110 may be in communication with receiver 160 and/or transmitter 170. Receiver 160 and transmitter 170 may be part of a transceiver. Receiver 160 and transmitter 170 may permit system 100 to communicate with one or more external devices wirelessly. Operation of receiver 160 and transmitter 170 may be controlled by processor 110 in accordance with user profiles 155. The data transmission rate and/or the power of transmitter 170 may be controlled for a reason such as to degrade a user experience (via slower loading of remote-hosted applications and/or web pages). A degraded user experience may be preferable for a reason such as to discourage a child from excessive use of the mobile device. The degraded user experience may encourage the child to pursue other activities not involving the mobile device (e.g., doing homework).

FIG. 2A illustrates an embodiment of a mobile device 200A configured to customize a user experience at least partially based on hand size. Mobile device 200A may contain system 100 of FIG. 1. Mobile device 200A may be a tablet computer, cellular phone (e.g., a smart phone), laptop computer, e-reader, personal digital assistant, gaming device, or some other type of mobile device. As illustrated, the front of mobile device 200A is shown with display 220 visible. Display 220 may be located on a front surface of a housing of mobile device 200A. Mobile device 200A may include housing 210. Coupled with housing 210 may be a plurality of proximity sensors, such as proximity sensors 212 and 214. Proximity sensors 120 may be arranged on the left and right sides (as illustrated) of the mobile device. As such, a user may be required to grasp these two sides of the mobile device simultaneously so that hand size may be measured. These may be the regions of mobile device 200A where a user typically holds the mobile device. Proximity sensors, such as proximity sensors 212 and 214, may be configured to detect when the user is gripping mobile device 200A; the proximity sensors may be configured to detect touch on the left and right edges of the mobile device, on the front, and/or on the back of the mobile devices. For example, proximity sensor 212 may be a single-electrode capacitive sensor that is configured to detect a change in capacitance between proximity sensor 212 and ground. In some embodiments, some or all proximity sensors may be dual-electrode proximity sensors having two electrodes.

A user's hand in the vicinity of proximity sensor 212 and/or a (second) hand in the vicinity of proximity sensor 214 may affect the magnitude of the capacitance measured by the respective proximity sensor. While nine proximity sensors are illustrated on each of the left and right of mobile device 200A, more or fewer proximity sensors may be present in other embodiments. Each proximity sensor is illustrated using dotted lines to indicate that the proximity sensor may not be visible, rather each proximity sensor may be concealed by housing 210 such that the proximity sensors are not externally visible. In some embodiments, proximity sensors may be arranged such as to be visible to users.

Figure 2C:
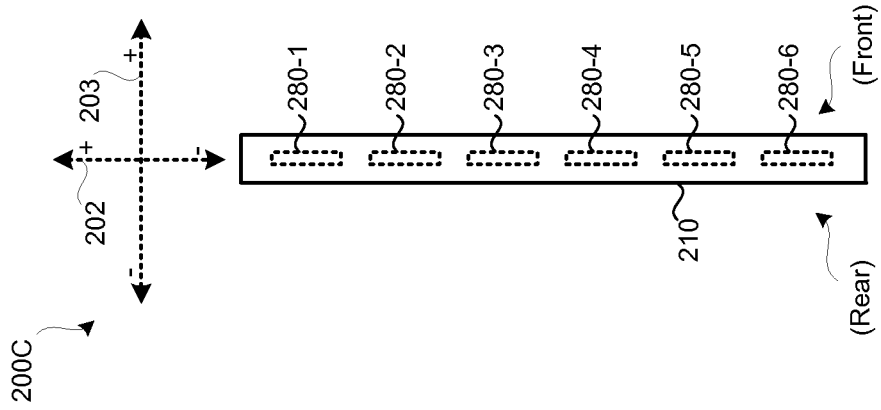
FIG. 2C illustrates an embodiment of a mobile device configured for customizing a configuration of a mobile device using hand size.

Also illustrated in FIG. 2A are imaginary axes, represented by dotted arrows. Such axes are in a coordinate system of the mobile device. The direction of acceleration as detected by one or more accelerometers of a mobile device may be interpreted in accordance with such a coordinate system. Referring to FIG. 2A, x-axis 201 is positive to the right (as illustrated) and negative to the left (as illustrated). Y-axis 202 is positive toward the top (as illustrated) of mobile device 200A, and negative toward the bottom (as illustrated). Z-axis 203 passes through mobile device 200A as illustrated in FIG. 2C.

Figure 2B:
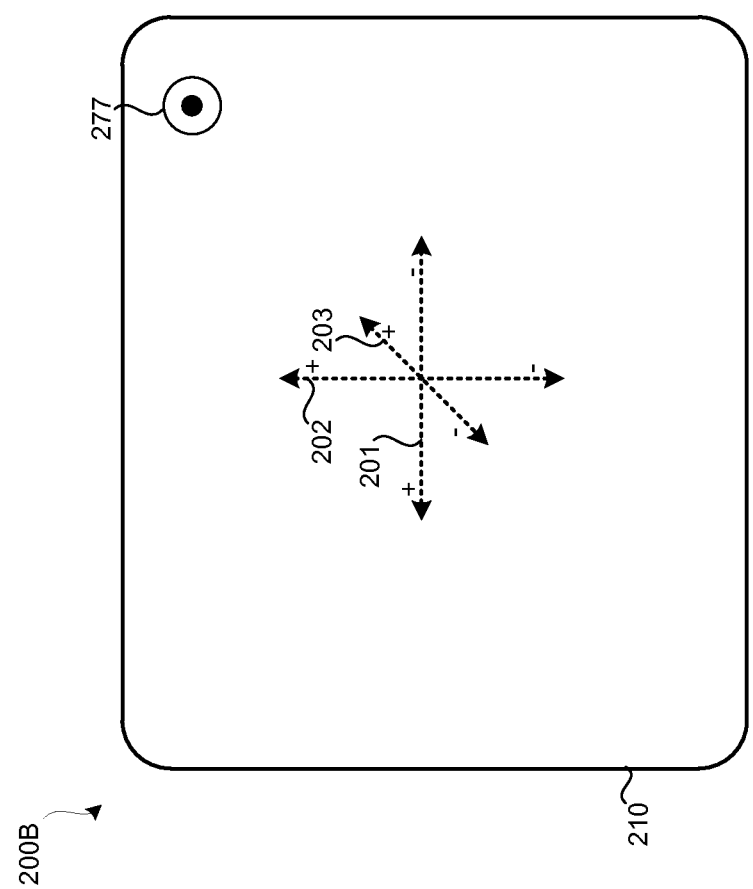
FIG. 2B illustrates an embodiment of a mobile device configured for customizing a configuration of a mobile device using hand size.

FIG. 2B illustrates an embodiment of a mobile device 200B configured for customizing a configuration of a mobile device using hand size. Mobile device 200B may represent mobile device 200A of FIG. 2A viewed from the rear. Mobile device 200B may not have proximity sensors to sense proximity to a triggering entity on the rear surface of housing 210. In some embodiments, proximity sensors may be present to additionally or alternatively measure finger length of the user. Mobile device 200B may have one or more cameras, such as camera 277, for facial recognition. Facial recognition may be used to supplement determination of a user using hand size and/or finger length.

The polarity of x-axis 201 and z-axis 203 appear reversed in FIG. 2B; this is because the mobile device is flipped and, as such, to remain in the coordinate system of the mobile device, these axes must be reoriented.

FIG. 2C illustrates an embodiment of a mobile device configured for customizing a configuration of a mobile device using hand size. Mobile device 200C may represent mobile device 200A of FIG. 2A and/or mobile device 200B of FIG. 2B viewed from a side. In some embodiments, proximity sensors 280 may be present along the side of mobile device 200C. A similar arrangement of proximity sensors may be present on the opposite side of mobile device 200C. Proximity sensors 280 and proximity sensors on the opposite side of mobile device 200C may, additionally or alternatively to the proximity sensors of FIG. 2A, be used to determine a user's hand size (which may be in form of hand width and/or palm width measurements). When gripping mobile device 200C, a user's hand width may be measured using proximity sensors 280 if the user's hand is in proximity to the illustrated side of mobile device 200C. FIG. 2C illustrates y-axis 202 and z-axis 203. In FIG. 2C, the front of the device containing display 220 (not shown) is on the right (as illustrated).

Figure 3A:
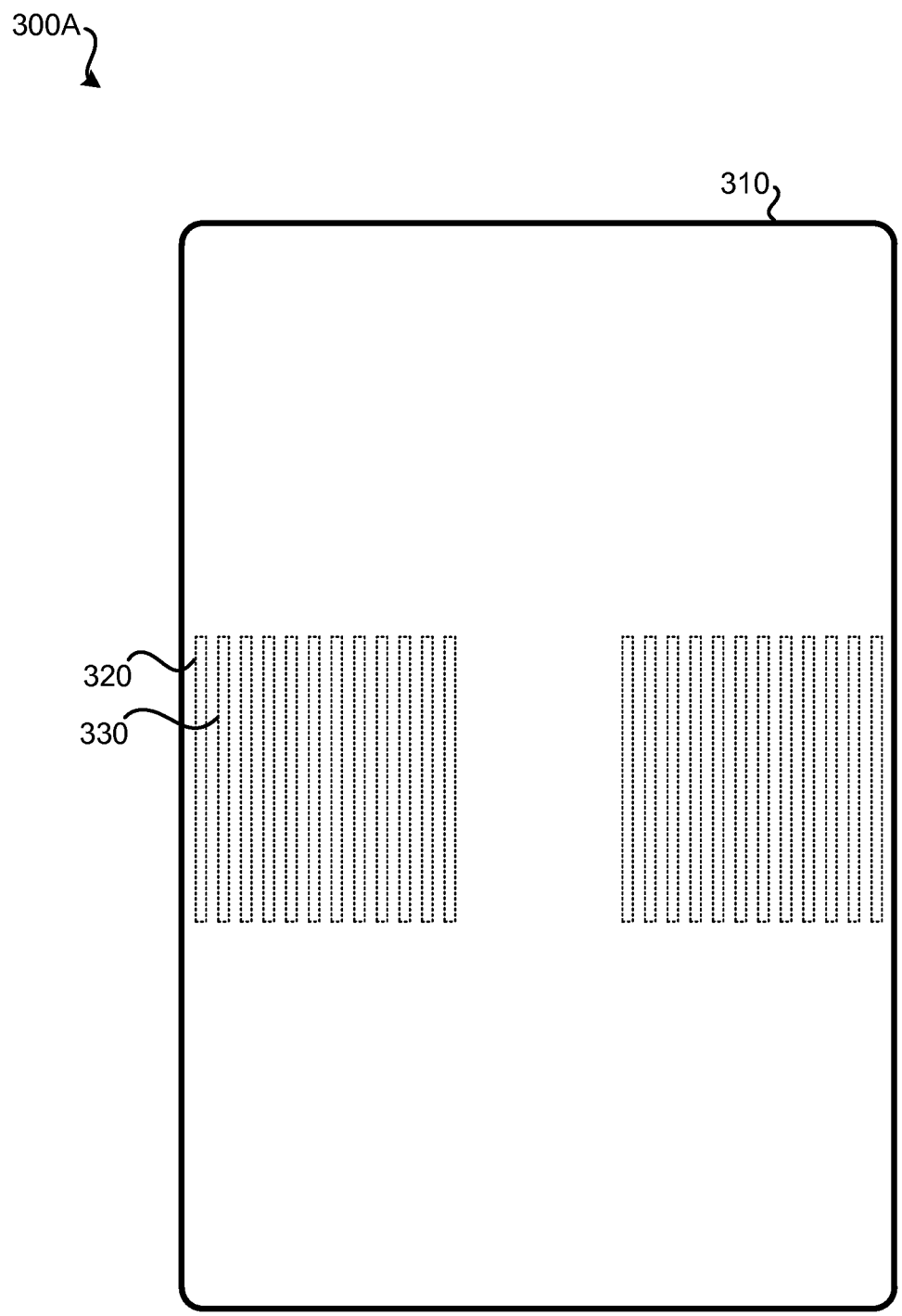
FIG. 3A illustrates an embodiment of a mobile device configured for customizing a configuration of a mobile device using finger length.
Figure 3B:
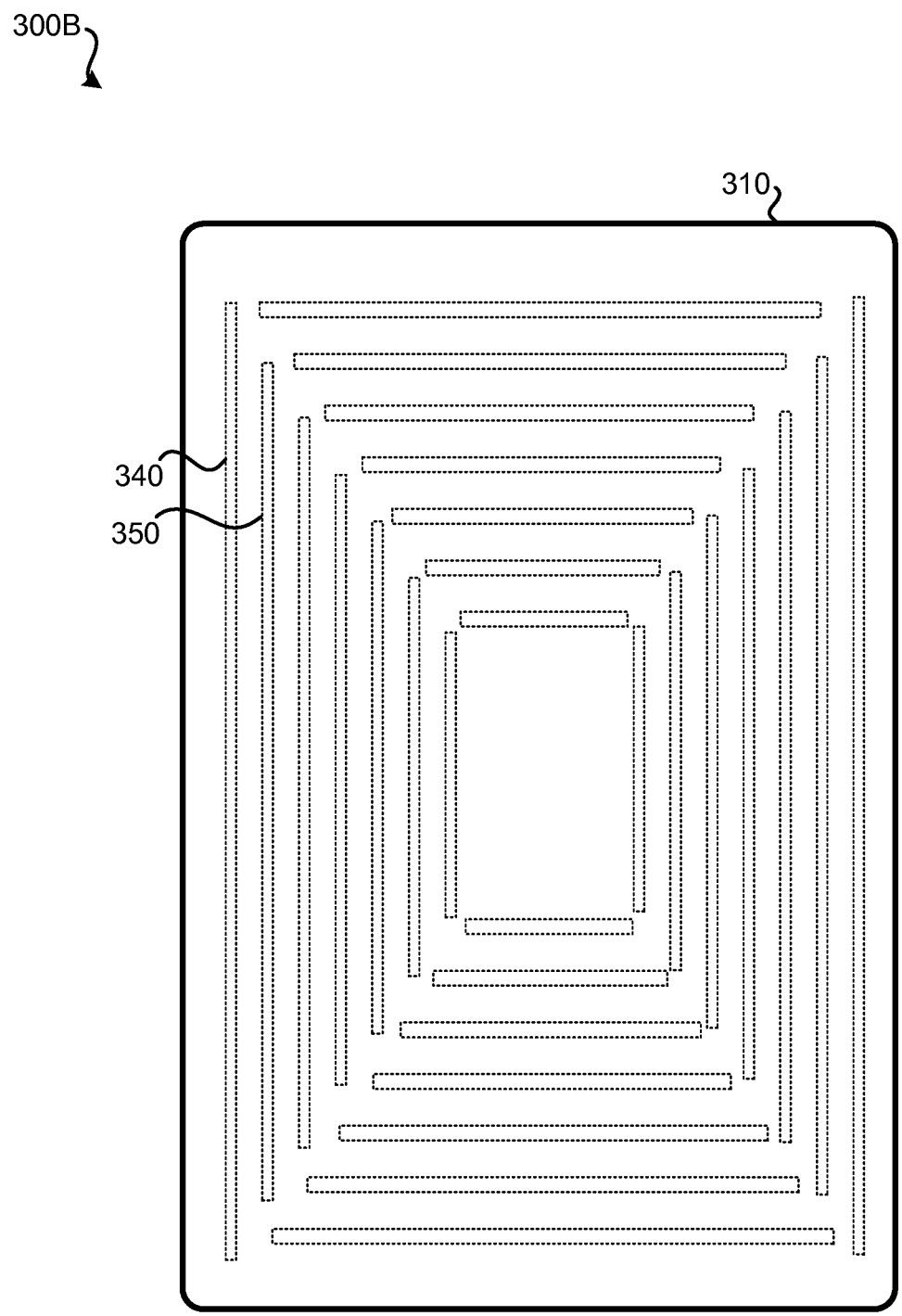
FIG. 3B illustrates another embodiment of a mobile device configured to customize a configuration based on finger length.
Figure 3C:
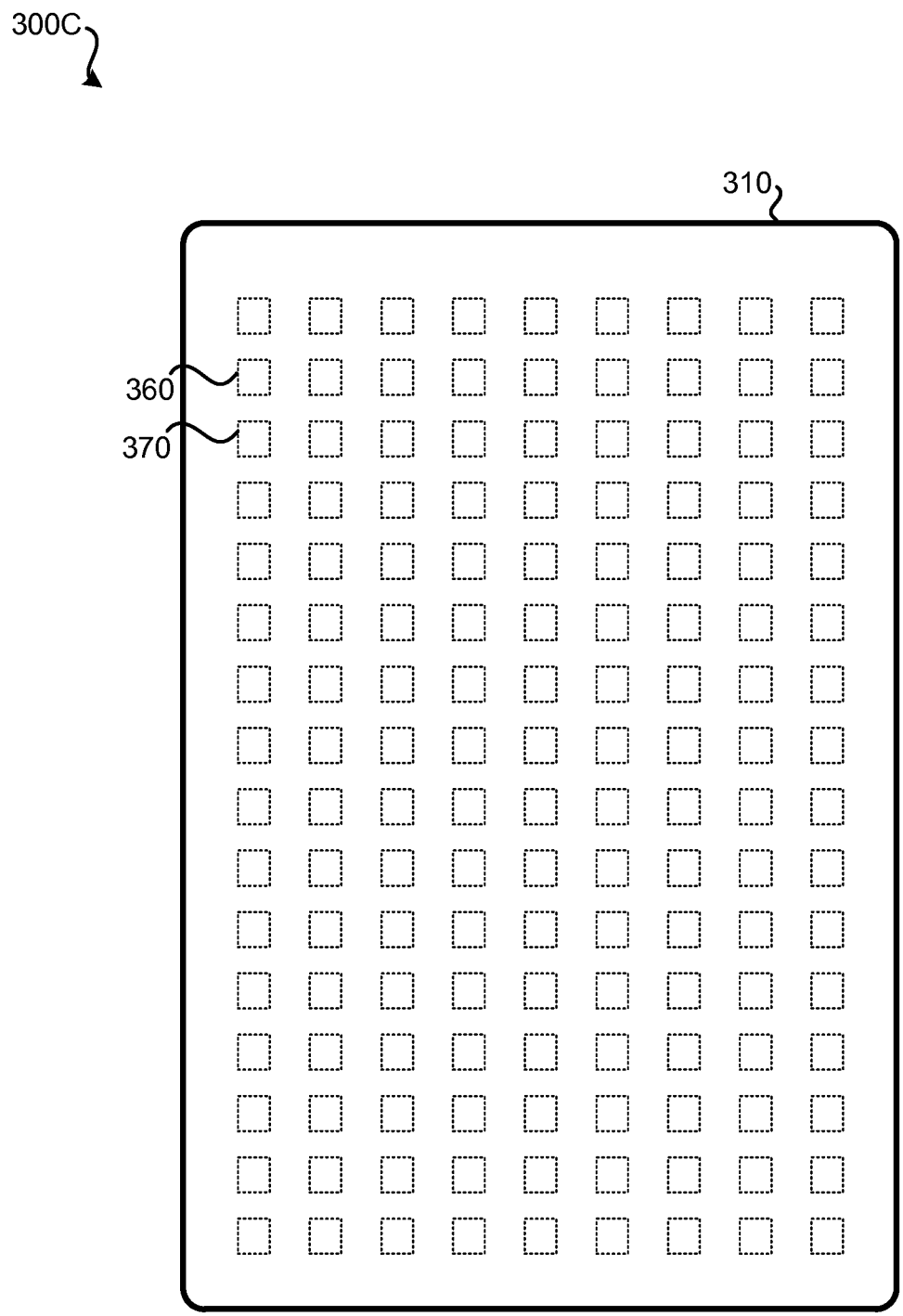
FIG. 3C illustrates another embodiment of a mobile device configured to customize a configuration based on finger length.

The proximity sensors of FIG. 2C (and of the side opposite to the side pictured in FIG. 2C) may contain only transmit proximity sensors, that is, transmit electrodes of dual-electrode proximity sensors. The receive proximity sensors (the other electrodes of the dual-electrode proximity sensors) may be located on the rear of the mobile device, such as illustrated in FIGS. 3A through 3C. The electrodes on opposite sides of the mobile device may transmit at different frequencies (for example, one side may be at 150 Hz while the other side is 75 Hz). As such, it may be able to be determined which side of the mobile device the hand is in contact with. This may be especially useful if the mobile device is small enough (e.g., a cellular phone, a small tablet) that a user's hand can reach across more than half of the rear of the mobile device. Such an arrangement may prevent a large hand from being measured as a small hand (because one or more fingers of the user's hand substantially reach across the rear of the device and contact the rear of the mobile device closer to the other side of the mobile device. By varying the frequency between different transmit proximity sensors on the opposite sides of the mobile device, it can be determined, using the proximity data, which side of the mobile device the user's hand is reaching from.

FIGS. 3A through 3C represent various arrangements of proximity sensors which may be present on the rear of a housing of a mobile device. Such arrangements of proximity sensors may be present on any of the previously discussed mobile devices, such as the mobile devices of FIGS. 2A-2C and may contain system 100 of FIG. 1. FIG. 3A illustrates an embodiment of a mobile device 300A configured for customizing a configuration of a mobile device using finger length. The mobile devices of FIGS. 2A-2C may also include such proximity sensors to permit determination of finger length.

Each dotted rectangle on housing 310 of mobile device 300A may represent a proximity sensor, such as proximity sensors 320 and 330. Each dotted rectangle may represent a single electrode capacitive proximity sensor. For example, proximity sensor 320 and proximity sensor 330 may represent single-electrode capacitive proximity sensors. Alternatively, each dotted rectangle may represent an electrode of a dual-electrode proximity sensor. For example, proximity sensor 320 and proximity sensor 330 may represent electrodes of a dual-electrode capacitive proximity sensor.

When mobile device 300A is gripped by a user in portrait mode, the longer the user's fingers, a greater number or different proximity sensors on the rear of housing 310 may output proximity data indicating proximity to a triggering entity (in this case, the user's fingers). As illustrated, proximity sensors may be located on the left and/or right side of the rear of mobile device 300A, to allow finger length to be determined for two hands simultaneously. The illustrated proximity sensors may be in addition to or instead of the proximity sensors presented in FIGS. 2A-2C.

FIG. 3B illustrates another embodiment of a mobile device 300B configured to customize a configuration based on finger length. Mobile device 300B may represent an embodiment of mobile device 200B of FIG. 2B. Housing 310 is illustrated from the rear. Each dotted rectangle may represent a proximity sensor. Each dotted rectangle may represent a single-electrode capacitive proximity sensor. For example, proximity sensor 340 and proximity sensor 350 may represent single-electrode capacitive proximity sensors. Alternatively, each dotted rectangle may represent an electrode of a dual-electrode proximity sensor. For example, proximity sensor 340 and proximity sensor 350 may represent electrodes of a dual-electrode capacitive proximity sensor.

When mobile device 300B is gripped by a user, the longer the user's fingers, a greater number or different proximity sensors on the rear of housing 310 may collect proximity data indicating proximity to a triggering entity (in this case, the user's fingers). As illustrated, proximity sensors may be located on the left and/or right side of the rear of mobile device 300B. Proximity sensors may also be located on the top and/or bottom of the rear of mobile device 300B as illustrated. As such, whether mobile device 300B is gripped in a landscape or portrait mode, the user's finger length may be determined The illustrated proximity sensors may be in addition to or instead of the proximity sensors presented in FIGS. 2A-2C.

FIG. 3C illustrates yet another embodiment of a mobile device 300C configured to customize a configuration based on finger length. Mobile device 300C may represent an embodiment of mobile device 200B of FIG. 2B. Housing 310 is illustrated from the rear. Each dotted rectangle may represent a proximity sensor. Each dotted rectangle may represent a single-electrode capacitive proximity sensor. For example, proximity sensor 360 and proximity sensor 370 may represent single-electrode capacitive proximity sensors. Alternatively, each dotted rectangle may represent an electrode of a dual-electrode proximity sensor. For example, proximity sensor 360 and proximity sensor 370 may represent electrodes of a dual-electrode capacitive proximity sensor. The number of proximity sensors present in each row and/or column may vary in other embodiments. Further, the arrangement of the proximity sensors may vary by embodiment.

When mobile device 300C is gripped by a user, the longer the user's fingers, a greater number or different proximity sensors on the rear of housing 310 may output proximity data indicating proximity to a triggering entity (in this case, the user's fingers). Proximity sensors, as arranged on housing 310 of mobile device 300C, may be used to measure finger length and/or hand size (e.g., hand width). Proximity sensors may also be located over the entire rear of housing 310, as illustrated. As such, whether mobile device 300C is gripped in a landscape or portrait mode, the user's finger length and/or hand size may be determined The illustrated proximity sensors may be in addition to or instead of the proximity sensors presented in FIGS. 2A-2C.

The embodiments of FIGS. 2 and 3 are shown as incorporated as part of a mobile device, however, in other embodiments, such proximity sensors may be incorporated as part of a housing that the mobile device is installed within. For instance, the proximity sensors may be part of an after-market case that the mobile device may be inserted into. Via wireless or wired communication, data from the proximity sensors may be transferred to the mobile device from the case. For instance, an application (e.g., "app") may be installed on the mobile device to utilize the proximity data acquired from the case, such as to control access to the mobile device. In some embodiments, at least some of the processing of the proximity data may be accomplished by a processing device within the case. Information derived from such processing, such as which user is attempting to access the mobile device, the size of the user's hand, and/or the length of the user's fingers may be transmitted to the mobile device.

Figure 4:
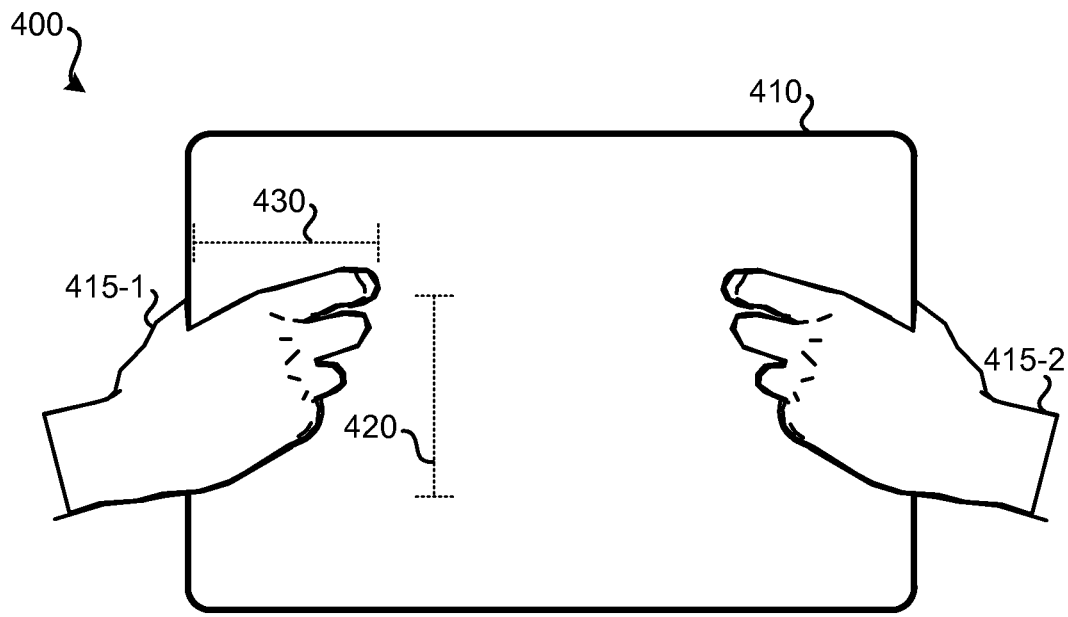
FIG. 4 illustrates an embodiment of a mobile device configured to customize a configuration based on hand size and/ or finger length of the user gripping the mobile device being gripped by a user with large hands.

FIG. 4 illustrates an embodiment 400 of a mobile device configured to customize a configuration based on hand size and/or finger length being gripped by a user. The mobile device of embodiment 400 may contain system 100 of FIG. 1 or some other system for customizing the configuration of a mobile device using hand size and/or finger length. Housing 410 of a mobile device may be held by user hands 415. Housing 410, which may represent the housing of mobile devices 200A, 200B, 200C, 300A, 300B, and/or 300C (or some other mobile device), is illustrated from the rear side, as in FIGS. 2B and 3A-3C. As such, FIG. 4 illustrates the back of a mobile device, such that a user views a display present on the opposite side (that is, the front side) of the mobile device. In some embodiments, to measure the size of a user's hands (e.g., the width of the user's hands) and/or the user's finger length, measurements for one hand are determined; in others, measurements for both hands are determined Determining the user's hand width may be based on the portion of each of the user's hands in contact with the side of housing 410. Measurement 420 indicates a region on housing 410 along each edge that hands 415 are in contact with. Such a measurement may be determined using proximity data gathered using one or more proximity sensors, such as those illustrated in FIG. 2A and 2C.

Alternatively or additionally, the finger length of one or both hands 415 of the user may be measured. In such embodiments, one or more proximity sensors may be placed on the back of a mobile device to aid in measuring the user's finger length. Measurement 430 at least approximately indicates a finger length of the user. Measurement 430 may be affected by how the user holds the mobile device, such as whether the user tends to curl one or more fingers while gripping the device. To determine measurement 430, proximity sensors may be arranged as presented in FIGS. 3A-3C, or in some other arrangement. While FIG. 4 illustrates housing 410 being gripped by two hands, in some embodiments, a grip using only one hand may be possible. Embodiments of some devices may only have proximity sensors on one side.

FIG. 5 illustrates an embodiment 500 of a mobile device configured to customize a configuration based on hand size and/or finger length being gripped by a user with smaller hands than in embodiment 400 of FIG. 4. Housing 510 of FIG. 5 may represent housing 410 present in FIG. 4 (that is, the same mobile device is being held by users with different size hands). In embodiment 500, a user with smaller hands is gripping housing 510. For example, hands 415 of FIG. 4 may represent the hands of adults while hands 515 represent the hands of a child. Measurement 520 indicates a region on housing 510 along each edge that hands 515 are in contact with. Measurement 520 may be considered a measurement of the user's hand width. Measurement 520 indicates a smaller distance than measurement 420 because hands 515 are in contact with (or in proximity to) a smaller area of housing 510 than hands 415 in relation to housing 410.

Additionally or alternatively, the user's finger length may be determined Measurement 530 indicates a measurement of the user's fingers. Measurement 530 may be affected by how the user holds the mobile device, such as whether the user tends to curl one or more fingers while gripping the device. In order to conduct an accurate measurement, the user may be required or instructed to uncurl one or more fingers to allow for a more accurate length measurement to be determined. Since measurement 530 is smaller than measurement 430, it may be determined that hand 515-1 belongs to a different person than hand 415-1. As such, a different user profile may be used by the mobile device for the user having hands 515 than with the user having hands 415. While FIG. 5 illustrates housing 510 being gripped by two hands, in some embodiments, a grip using only one hand may be possible. For a one handed grip, hand size and/or finger length may be determined for only the one hand.

Additionally, hands 515 are gripping housing 510 in a lower region compared with hands 415 of FIG. 4. Hands 515 are also gripping housing 510 at a different angle than hands 415 of FIG. 4. In addition to hand size and finger length, such grip characteristics may be used to identify the user and/or a user profile associated with the user.

FIG. 6 illustrates an embodiment 600 of a mobile device configured to customize a configuration based on finger length and/or hand size. The device of embodiment 600 may be illustrated in FIGS. 2B and 3B. The mobile device of embodiment 600 may include system 100 of FIG. 1 or some other system configured to customize a configuration based on finger length and/or hand size. For demonstration purposes, two different sized hands are illustrated as gripping the mobile device of embodiment 600. It should be understood that in actual use conditions a single user would be gripping the mobile device, thus the two hand sizes would likely be approximately the same. Hand 515-1 is smaller than hand 415-2 and has shorter fingers. As such, when hand 515-1 grasps housing 610, fewer proximity sensors on housing 610 are triggered. In this case, hand 515-1 is in contact with three proximity sensors. Hand 415-2, having longer fingers, triggers a greater number of proximity sensors on housing 610. Hand 415-2 is in close proximity to five proximity sensors while hand 515-1 is in close proximity to three proximity sensors. As such, the number of triggered proximity sensors by the length of a user's fingers (on one or both hands) may be used to select a particular user profile that determines how the mobile device is customized for the user.

FIG. 7 illustrates an embodiment of a method 700 for configuring a system that customizes a configuration of a mobile device based on hand size. Method 700 may be performed by a mobile device, such as the mobile devices presented in relation to FIGS. 2 though 6. Such mobile devices may contain a system for customizing a configuration of the mobile device based on hand size and/or finger length, such as system 100 of FIG. 1. Means for performing each step of method 700 may include a mobile device. More specifically, the means for performing each step of method 700 may include system 100 of FIG. 1, a similar system, and/or a computer system, such as computer system 1000 of FIG. 10.

At step 710, a configuration mode may be entered on the mobile device. The configuration mode may be entered based on a user providing input to the mobile device that indicates the mobile device should be configured to customize the configuration based on the user's hand size (e.g., hand width), finger length, and/or grip characteristics.

At step 720, a user may be prompted to grasp the mobile device. The user may be prompted to grasp the mobile device in the manner the user will typically be gripping the mobile device during use. This may involve grasping the mobile device with one or two hands. If finger length is to be used, the user may be instructed to uncurl his or her fingers, such that at least the finger or fingers to be measured are approximately straight. At step 720, the user may grasp the mobile device.

At step 730, proximity data may be collected by the mobile device using multiple proximity sensors. Data gathered from each of the proximity sensors may indicate whether a triggering entity is in contact with or near the proximity sensor (collectively referred to as being proximate to the proximity sensor). Based upon a magnitude of the proximity data, the presence of a triggering entity, such as part of a user's hand or finger, can be determined A step 740, using the proximity data collected at step 730, a hand size (e.g., hand width), finger length, and/or grip of the user may be determined At step 750, hand size, finger length, and/or grip information may be stored as part of a user profile. Determining the user's hand size may be based on the amount of contact that the user's hand(s) make with the housing of the mobile device, as determined using the proximity data. For example, the distance along a side of the mobile device that the user's hand contacts the housing may be used as the user's hand width. (The larger the hand, the more of the hand that may be expected to be in contact with the side of the housing of the mobile device.) Such information for the user may be stored as part of a user profile.

At step 760, as part of the user profile, various characteristics may be stored, such as application permissions, an order of applications to be displayed, permitted data transmission rates, and/or permitted data transmission power levels as the characteristics described in relation to user profiles 155 of FIG. 1. These characteristics may be used to customize the configuration of the mobile device for the user. Additionally, as part of the user profile, a username, password, and/or image of the user may be stored to serve as additional ways of accessing the user profile.

At step 770, it may be determined whether an additional user will be using the mobile device and should be identified by hand size. For example, at step 770, a prompt may be presented by the mobile device that inquires whether the mobile device should be configured for an additional user. If a "yes" response is received, method 700 may return to step 720 such that steps 720 through 760 may be performed for the additional user. If a "no" response is received, method 700 may proceed to step 780.

At step 780, it may be determined whether each of the users for which hand size, finger length, and/or grip information was acquired can be differentiated on the basis of hand size, finger length, and/or grip information. For example, if finger length data was received for three users, a father, a mother, and a child, each user's finger length may be significantly different. As such, the mobile device may be able to determine which user is accessing the mobile device based on the finger length. As such, method 700 may proceed to step 785. Hand size, finger length, and/or grip information may be used individually or together to determine which user is attempting to access the mobile device.

If, at step 780, users cannot be differentiated based on hand size, finger length, and/or grip characteristics, method 700 may proceed to step 790. For example, in a situation where a mother's and child's hands are similar in size, it may not be possible to differentiate the users based solely on finger length. As such, an alternate arrangement for accessing the mobile device may be necessary in place of or in addition to the determination of finger length. At step 790, the user may be prompted that hand size, finger length, and/or grip characteristics will not be sufficient alone to identify individual users. At step 795, additional login requirements, such as a username and password, may be configured. Such an additional login procedure may be conducted in addition to detection of hand size, finger length, and/or grip characteristics.

Rather than method 700 being used to configure access to a mobile device for individual users, a similar method may be used to configure access to the mobile device for classes of users. Such an arrangement may be preferable when multiple users with similar small children, which may be defined as users having a hand size or finger length below a particular threshold, can use the same user profile. As such, a user profile may be created, or predefined, for user classes such as adults, teenagers, and other children by defining ranges of hand sizes and/or finger lengths for profiles, along with how the configuration of the mobile device will be customized for each user class.

FIG. 8 illustrates an embodiment of a method for customizing a configuration of a mobile device based on hand size being gripped by a user. Method 800 may be performed by a mobile device, such as the mobile devices presented in relation to FIGS. 2 though 6. Such mobile devices may contain a system for customizing a configuration of the mobile device based on hand size and/or finger length, such as system 100 of FIG. 1. Means for performing each step of method 800 may include a mobile device. More specifically, the means for performing each step of method 800 may include system 100 of FIG. 1, a similar system, and/or a computer system, such as computer system 1000 of FIG. 10. While method 800 focuses on the use of finger length to customize the configuration of a mobile device, it should be understood that in addition to finger length, or alternatively to finger length, hand size (e.g., hand width) may be used. Grip characteristics may also additionally or alternatively be used.

At step 810, proximity data may be collected using one or more proximity sensors. Data gathered from each of the proximity sensors may indicate whether a triggering entity is in contact with or near the proximity sensor (collectively referred to as being proximate to the proximity sensor). Based upon a magnitude of the proximity data, the presence of a triggering entity, such as part of a user's hand or finger, can be determined At step 820, it may be determined that a user has gripped the mobile device The determination may include determining if the user has gripped the mobile device with one or two hands. This determination may be at least partially based on the proximity data collected at step 810. Additionally, acceleration data, such as from an accelerometer, may be used to determine if the mobile device is being gripped. In order to determine that the user has gripped the mobile device and avoid false positives, it may be necessary for the user to grip the mobile device with two hands, such as with one hand on either side (e.g., the left and right or the top and bottom) of the mobile device. While in a sleep or hibernation mode, the mobile device may be running an algorithm that analyzes proximity data to determine if a user has grasped the device. The algorithm may cease being executed once a user has grasped the device until the device is again placed in sleep or hibernation mode.

At step 830, the finger length of the user gripping the mobile device may be determined Determining the finger length of the user may involve determining how far one or more fingers of the user extends on the rear of the housing of the mobile device, such as illustrated in FIG. 6. If, rather than finger length, hand size, such as hand width, is used, determining the hand size of the user may mean determining the area or a length of the user's hands in contact with or in proximity to the housing of the mobile device or calculating the user's hand size based on the area or length of the user's hand(s) in contact with or in proximity to the housing of the mobile device. The determination of finger length of the user at step 830 may be computed for each hand of the user (assuming the user is gripping the device with two hands). Each measured finger may be required to be within a certain range of tolerance of stored finger length measurements of a user profile stored by the mobile device (or remotely). In some embodiments, the measurement of each finger length of the user may be averaged to determine an average finger length for the user.

Before, at the same time of step 830, or after, another form of identity authentication may be performed, such as facial recognition using a camera. Such a secondary form of identity authentication may prevent another person with fingers of similar length from being confused with a user of the device. Additionally, a gesture, such as how the mobile device is picked up (such as the user picking the mobile device up, putting it down, and picking it back up), may be used to identify the user. Each such method of identifying a user may be given a weight and collectively used to identify the user.

Further, past usage patterns may be used to help identify a user. For example, if a first user typically uses a mobile device at noon on Wednesday, at that time the mobile device may select a user profile associated with the first user despite another user being associated with the same hand size.

At step 840, the configuration of the mobile device may be customized at least partially based on finger length. This customization of the configuration may involve loading a user profile stored by the mobile device. The user profile may be stored for a particular user or a class of users. This user profile may have been previously configured during a configuration process, such as described in relation to method 700 of FIG. 7. The mobile device may remain as configured at step 840 for as long as the mobile device is actively being used. For example, after the mobile device has been placed down or is no longer in contact with at least one user hand, the mobile device may be reconfigured based on hand size by repeating method 800 when the mobile device is gripped next. The mobile device may reassess who a user is at or after step 730. For example, following step 720, a user may be provided a user profile for an unidentified adult. After performing facial recognition, the user interface may be reconfigured for a particular user.

As part of the customization of the mobile device, telephone calls and/or text messages (e.g., SMS, MMS) that are typically sent to a user's mobile phone may be routed to the mobile device being held by the user. For example, if a particular user is detected as gripping the mobile device, and, possibly, the user's mobile phone indicates it is not being gripped or otherwise held, telephone calls and/or text messages may be routed to the mobile device. In such an instance, the user's mobile phone may not ring and/or vibrate. Further details regarding this process may be found in previously filed U.S. patent application Ser. No. 12/851,413, entitled "Communication Management Utilizing Destination Device User Presence Probability," filed Aug. 5, 2010, which is hereby incorporated by reference for all purposes.

FIG. 9 illustrates an embodiment of a method 900 for customizing the configuration of a mobile device based on hand size and/or finger length of the user gripping the mobile device. Method 900 may be performed by a mobile device, such as mobile devices of FIGS. 2A-2C and/or FIGS. 3A-3C. Such mobile devices may contain a system for customizing a user experience based on hand size, such as system 100 of FIG. 1. Method 900 may be performed after method 700 has been used to configure a mobile device with user profiles for particular users or classes of users. Method 900 may represent a more detailed embodiment of method 800. Means for performing each step of method 900 may include a mobile device. More specifically, the means for performing each step of method 900 may include system 100 of FIG. 1, a similar system, and/or a computer system, such as computer system 1000 of FIG. 10. While method 900 focuses on the use of finger length to customize the configuration of a mobile device, it should be understood that in addition to finger length, or alternatively to finger length, hand size (e.g., hand width) may be used. Grip characteristics may also additionally or alternatively be used.

At step 910, proximity data may be collected using one or more proximity sensors of the mobile device. Proximity data gathered from each of the proximity sensors may indicate whether a triggering entity is in proximity. The proximity data may indicate a magnitude. This magnitude may be used to determine how close and/or how big a triggering entity is. Based upon a magnitude of the proximity data, the presence of a triggering entity, such as part of a user's hand or finger, can be determined In some embodiments, a sensitivity level may be set for the mobile device. The sensitivity level may indicate a threshold of magnitude, below which a triggering entity is not considered proximate to the mobile device.

At step 920, the mobile device may determine whether the user has gripped the mobile device. Such detection of the user gripping the mobile device may involve a processor of the mobile device receiving and analyzing the proximity data collected from one or more proximity sensors at step 910. In order to determine that the user has gripped the mobile device and to avoid false positives, it may be necessary for the user to grip the mobile device with two hands, such as with one hand on either side (e.g., the left and right or the top and bottom) of the mobile device. As such, in order to initialize a login process, the user may be required to grip the mobile device with two hands; thus, possibly also requiring the user to place both hands in positions where hand width and/or finger length can be measured.

At step 930, the finger length of the user may be determined Determining the finger length of the user may involve measuring a length of one or more fingers—such as one finger on each hand—as they contact the rear of the housing of the mobile device. The user may be instructed to uncurl the fingers to be measured, such that an accurate measurement of each finger can be obtained. The proximity data collected at step 910 may be used to determine the finger length of the user. Each measured finger length may be required to be within a certain range of tolerance of stored finger length measurements of a user profile stored by the mobile device (or remotely). In some embodiments, the measurement of each finger length of the user may be averaged to determine an average finger length for the user.

In some embodiments, in addition to finger length or as an alternate to finger length, the user's hand size may be determined. Determining the hand size of the user may mean determining the area or a length of the user's hands in contact with or in proximity to the housing of the mobile device or calculating the user's hand size based on the area or length of the user's hand(s) in contact with or in proximity to the housing of the mobile device. The determination of hand size of the user at step 930 may be computed for each hand of the user (assuming the user is gripping the device for two hands). Each hand may be required to be within a certain range of tolerance of stored hand size measurements of a user profile stored by the mobile device (or remotely). In some embodiments, the measurement of each hand of the user may be averaged to determine an average hand size for the user.

At step 940, one or more user profiles may be selected. The user profiles may be selected from a set of multiple user profiles. Each user profile of the set may be for a particular user or may be for a class of users. The set of user profiles may define user profiles for specific users as well as user profiles for classes of users. The user profiles may define characteristics to be applied to the mobile device while the user is using the mobile device. The one or more user profiles selected at step 940 may have been preconfigured on the mobile device before purchase or, such as via method 700, the user profile may have been created and/or customized by a user. If a single user profile matches the finger length determined at step 930, method 900 may proceed to step 960. If multiple user profiles match the determined finger length, method 900 may proceed to step 950.

At step 950, one or more additional authentication procedures may be used to determine which of the selected user profiles is to be used to customize the configuration of the mobile device. Additional authentication procedures may involve facial recognition. As such, a picture of the user gripping the mobile device may be captured and compared to images linked with each selected user profile. The image of the user profile that matches the captured image the closest may result in the corresponding user profile being loaded. Other additional authentication procedures include: the user being required to provide a password, the user being required to perform a gesture, voice recognition, and analyzing how the mobile device is being gripped. Following the additional authentication of step 950, the one or more additional authentication procedures may permit a single user profile to be selected from the multiple user profiles selected at step 940.

Following the user profile being selected, the operation of the mobile device may be customized in accordance with the user profile. In the illustrated embodiment of method 900, two additional steps are performed, steps 960 and 970, to customize the mobile device. It should be understood that these steps of customizing the mobile device are for example purposes only; in other embodiments, the mobile device may be customized differently.

The configuration of the mobile device may be customized in accordance with the selected user profile. The mobile device may remain as configured at steps 960 and 970 for as long as the mobile device is actively being used by the user. For example, after the mobile device has been placed down or is no longer in contact with at least one hand of the user for a predetermined period of time, the mobile device may be reconfigured based on hand size by repeating method 900 when the mobile device is gripped next. Customizing the configuration of the mobile device may include: presenting only a subset of available functions (e.g., applications) for user by the user, restricting access to the internet, arranging icons for functions of the mobile device is a particular order, adjusting device preferences (e.g., screen brightness, audio volume), adjusting maximum data transmission and/or reception rates, adjusting transmit power, and/or enforcing a use time and/or data cap.

Steps 960 and 970 may represent various ways of customizing the mobile device. Depending on the user profile, a greater or fewer number of steps may be present to customize the configuration of the mobile device. At step 960, the data transmission rate and/or the power of data transmission of the mobile device may be limited (e.g., not permitted to exceed a maximum threshold) in accordance with the user profile. This may make the mobile device intentionally less desirable to use, such as to make watching streaming video or games less desirable to a child. At step 970, the presentation of the user interface, such as the arrangement of icons related to functions of the mobile device and/or which functions are presented to the user may be customized. As such, based on the user's finger length and associated user profile (and possibly other login information), the user interface of the mobile device may be configured for a particular user.

As an example of method 900, consider a family having a father, a mother, a young child, and a teenage son. The father and teenage son have the longest fingers, both approximately the same length. The young child has the shortest fingers, and the mother's fingers are longer than the young child, but shorter than the teenage son's and father's. Method 700 may have been previously performed to link user profiles with each of these users. An administrator, such as one of the users, may define some or all characteristics of the other users' profiles. For example, the father or mother may set data rate limitations on the young child's user profile.

When the young child picks up the mobile device, proximity data may be collected at step 910. At step 920, the mobile device may determine that it is being gripped. At step 930, the finger length of the young child may be measured, possibly on both hands. At step 940, the user profile of the young child may be selected. Since the young child has the shortest fingers and no other user has fingers of a similar short length, method 900 may proceed to step 960 from step 940. Based on the young child user profile, the configuration of the mobile device may be customized For example, the data transmission rate of the mobile device may be limited, and only functions approved by the young child's parents may be presented for use.

When the teenage son picks up the mobile device, proximity data may be collected at step 910. At step 920, the mobile device may determine that it is being gripped. At step 930, the finger length of the teenage son may be measured. At step 940, since the teenage son and the father have similar finger lengths, method 900 may proceed to step 950. At step 950, additional authentication may be performed in the form of an image being captured of the user. Based on the finger length and the image, the teenage son may be identified. Following identification of the teenage son, the mobile device may be customized for his use in accordance with the teenage son's user profile.

FIG. 10 illustrates an embodiment of a computer system. Computer system 1000 can represent some of the components of the mobile devices and systems discussed in this application. FIG. 10 provides a schematic illustration of one embodiment of a computer system 1000 that can perform the methods provided by various embodiments. It should be noted that FIG. 10 is meant only to provide a generalized illustration of various components, any or all of which may be utilized as appropriate. FIG. 10, therefore, broadly illustrates how individual system elements may be implemented in a relatively separated or relatively more integrated manner.

The computer system 1000 is shown comprising hardware elements that can be electrically coupled via a bus 1005 (or may otherwise be in communication, as appropriate). The hardware elements may include one or more processors 1010, including without limitation one or more general-purpose processors and/or one or more special-purpose processors (such as digital signal processing chips, graphics acceleration processors, and/or the like); one or more input devices 1015, which can include without limitation a mouse, a keyboard, and/or the like; and one or more output devices 1020, which can include without limitation a display device, a printer, and/or the like.

The computer system 1000 may further include (and/or be in communication with) one or more non-transitory storage devices 1025, which can comprise, without limitation, local and/or network accessible storage, and/or can include, without limitation, a disk drive, a drive array, an optical storage device, a solid-state storage device, such as a random access memory ("RAM") and/or a read-only memory ("ROM"), which can be programmable, flash-updateable, and/or the like. Such storage devices may be configured to implement any appropriate data stores, including without limitation, various file systems, database structures, and/or the like.

The computer system 1000 might also include a communications subsystem 1030, which can include without limitation a modem, a network card (wireless or wired), an infrared communication device, a wireless communication device and/or chipset (such as a Bluetooth™ device, an 802.11 device, a WiFi device, a WiMax device, cellular communication facilities, etc.), and/or the like. The communications subsystem 1030 may permit data to be exchanged with a network (such as the network described below, to name one example), other computer systems, and/or any other devices described herein. In many embodiments, the computer system 1000 will further comprise a working memory 1035, which can include a RAM or ROM device, as described above.

The computer system 1000 also can comprise software elements, shown as being currently located within the working memory 1035, including an operating system 1040, device drivers, executable libraries, and/or other code, such as one or more application programs 1045, which may comprise computer programs provided by various embodiments, and/or may be designed to implement methods, and/or configure systems provided by other embodiments, as described herein. Merely by way of example, one or more procedures described with respect to the method(s) discussed above might be implemented as code and/or instructions executable by a computer (and/or a processor within a computer); in an aspect, then, such code and/or instructions can be used to configure and/or adapt a general purpose computer (or other device) to perform one or more operations in accordance with the described methods.

A set of these instructions and/or code might be stored on a non-transitory computer-readable storage medium, such as the storage device(s) 1025 described above. In some cases, the storage medium might be incorporated within a computer system, such as computer system 1000. In other embodiments, the storage medium might be separate from a computer system (e.g., a removable medium, such as a compact disc), and/or provided in an installation package, such that the storage medium can be used to program, configure, and/or adapt a general purpose computer with the instructions/code stored thereon. These instructions might take the form of executable code, which is executable by the computer system 1000 and/or might take the form of source and/or installable code, which, upon compilation and/or installation on the computer system 1000 (e.g., using any of a variety of generally available compilers, installation programs, compression/decompression utilities, etc.), then takes the form of executable code.

It will be apparent to those skilled in the art that substantial variations may be made in accordance with specific requirements. For example, customized hardware might also be used, and/or particular elements might be implemented in hardware, software (including portable software, such as applets, etc.), or both. Further, connection to other computing devices such as network input/output devices may be employed.

As mentioned above, in one aspect, some embodiments may employ a computer system (such as the computer system 1000) to perform methods in accordance with various embodiments of the invention. According to a set of embodiments, some or all of the procedures of such methods are performed by the computer system 1000 in response to processor 1010 executing one or more sequences of one or more instructions (which might be incorporated into the operating system 1040 and/or other code, such as an application program 1045) contained in the working memory 1035. Such instructions may be read into the working memory 1035 from another computer-readable medium, such as one or more of the storage device(s) 1025. Merely by way of example, execution of the sequences of instructions contained in the working memory 1035 might cause the processor(s) 1010 to perform one or more procedures of the methods described herein.

The terms "machine-readable medium" and "computer-readable medium," as used herein, refer to any medium that participates in providing data that causes a machine to operate in a specific fashion. In an embodiment implemented using the computer system 1000, various computer-readable media might be involved in providing instructions/code to processor(s) 1010 for execution and/or might be used to store and/or carry such instructions/code. In many implementations, a computer-readable medium is a physical and/or tangible storage medium. Such a medium may take the form of a non-volatile media or volatile media. Non-volatile media include, for example, optical and/or magnetic disks, such as the storage device(s) 1025. Volatile media include, without limitation, dynamic memory, such as the working memory 1035.

Common forms of physical and/or tangible computer-readable media include, for example, a floppy disk, a flexible disk, hard disk, magnetic tape, or any other magnetic medium, a CD-ROM, any other optical medium, punchcards, papertape, any other physical medium with patterns of holes, a RAM, a PROM, EPROM, a FLASH-EPROM, any other memory chip or cartridge, or any other medium from which a computer can read instructions and/or code.

Various forms of computer-readable media may be involved in carrying one or more sequences of one or more instructions to the processor(s) 1010 for execution. Merely by way of example, the instructions may initially be carried on a magnetic disk and/or optical disc of a remote computer. A remote computer might load the instructions into its dynamic memory and send the instructions as signals over a transmission medium to be received and/or executed by the computer system 1000.

The communications subsystem 1030 (and/or components thereof) generally will receive signals, and the bus 1005 then might carry the signals (and/or the data, instructions, etc. carried by the signals) to the working memory 1035, from which the processor(s) 1010 retrieves and executes the instructions. The instructions received by the working memory 1035 may optionally be stored on a storage device 1025 either before or after execution by the processor(s) 1010.

The methods, systems, and devices discussed above are examples. Various configurations may omit, substitute, or add various procedures or components as appropriate. For instance, in alternative configurations, the methods may be performed in an order different from that described, and/or various stages may be added, omitted, and/or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Specific details are given in the description to provide a thorough understanding of example configurations (including implementations). However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the spirit or scope of the disclosure.

Also, configurations may be described as a process which is depicted as a flow diagram or block diagram. Although each may describe the operations as a sequential process, many of the operations can be performed in parallel or concurrently. In addition, the order of the operations may be rearranged. A process may have additional steps not included in the figure. Furthermore, examples of the methods may be implemented by hardware, software, firmware, middleware, microcode, hardware description languages, or any combination thereof. When implemented in software, firmware, middleware, or microcode, the program code or code segments to perform the necessary tasks may be stored in a non-transitory computer-readable medium such as a storage medium. Processors may perform the described tasks.

Having described several example configurations, various modifications, alternative constructions, and equivalents may be used without departing from the spirit of the disclosure. For example, the above elements may be components of a larger system, wherein other rules may take precedence over or otherwise modify the application of the invention. Also, a number of steps may be undertaken before, during, or after the above elements are considered. Accordingly, the above description does not bound the scope of the claims.

What is claimed is:

1. A method for customizing a configuration of a mobile device, the method comprising:
    collecting, by the mobile device, proximity data;
    determining, by the mobile device, that a user has gripped the mobile device based on the proximity data;

determining, by the mobile device, a hand size of the user using the proximity data;

determining, by the mobile device, whether the user is an adult or a child based on the hand size; and customizing, by the mobile device, the configuration of the mobile device at least partially based on whether the user is the adult or the child.

2. The method for customizing the configuration of the mobile device of claim 1, wherein:

customizing, by the mobile device, the configuration of the mobile device comprises limiting a data transmission rate of the mobile device.

3. The method for customizing the configuration of the mobile device of claim 1, further comprising:

receiving, by the mobile device, a text message routed to the mobile device at least partially based on the user gripping the mobile device, wherein a mobile phone linked with the user does not ring or vibrate in response to the text message.

4. The method for customizing the configuration of the mobile device of claim 1, wherein determining that the user has gripped the mobile device based on the proximity data comprises:

using the proximity data, determining, by the mobile device, that the user has gripped the mobile device with two hands.

5. The method for customizing the configuration of the mobile device of claim 4, wherein determining, by the mobile device, the hand size of the user using the proximity data comprises:

determining, by the mobile device, a first hand size of a left hand of the user and a second hand size of a right hand of the user.

6. The method for customizing the configuration of the mobile device of claim 4, wherein:

the mobile device comprises:
a housing, wherein:
the housing has a front surface and a rear surface; and
the front surface comprises a display; and
the proximity data is collected by the mobile device using a plurality of proximity sensors arranged on the rear surface of the housing of the mobile device.

7. The method for customizing the configuration of the mobile device of claim 6, wherein:

the mobile device is configured to measure a first hand size of the user on a first hand and a second hand size of a second hand when the first hand of the user grips a first side of the mobile device and the second hand of the user grips a second side of the mobile device; and the first hand of the user and the second hand of the user simultaneously grip the mobile device.

8. The method for customizing the configuration of the mobile device of claim 1, wherein:

customizing, by the mobile device, the configuration of the mobile device comprises selecting functions from a set of functions available to the user at least partially based on the hand size of the user.

9. The method for customizing the configuration of the mobile device of claim 1, further comprising:

receiving, by the mobile device, proximity data for each user of a plurality of users, wherein:
the plurality of users comprises the user; and
the proximity data corresponding to each user is used to determine the hand size for each user of the plurality of users; and storing, by the mobile device, a user profile for each user, wherein the user profile identifies the hand size for the corresponding user.

10. A mobile device configured to customize a configuration, the mobile device comprising:

a housing comprising:
a front surface comprising a display; and
a rear surface;
two pairs of capacitive proximity sensors configured to:
collect proximity data that indicates proximity to a triggering entity;
a processor; and
a memory communicatively coupled with and readable by one or more processors and having stored therein processor-readable instructions which, when executed by the one or more processors, cause the one or more processors to:
determine that a user has gripped the mobile device based on the proximity data;
determine a hand size of the user using the proximity data;
determine whether the user is an adult or a child based on the hand size and
customize the configuration of the mobile device at least partially based on whether the user is the adult or the child.

11. The mobile device configured to customize the configuration of claim 10, further comprising:

a transmitter, wherein a data transmission rate of the transmitter is adjusted at least partially based on the configuration of the mobile device customized.

12. The mobile device configured to customize the configuration of claim 10, wherein the processor-readable instructions further comprise processor-readable instructions configured to cause the one or more processors to:

present a text message routed to the mobile device at least partially based on the user gripping the mobile device, wherein a mobile phone linked with the user does not ring or vibrate in response to the text message.

13. The mobile device configured to customize the configuration of claim 10, wherein the processor-readable instructions that cause the one or more processors to determine that a user has gripped the mobile device based on the proximity data further comprises processor-readable instructions that cause the one or more processors to, using the proximity data, determine that the user has gripped the mobile device with two hands.

14. The mobile device configured to customize the configuration of claim 13, wherein the processor-readable instructions configured to cause to the one or more processors to determine the hand size of the user using the proximity data comprises processor-readable instructions configured to cause the one or more processors to:

determine a first hand size of a left hand of the user and a second hand size of a right hand of the user.

15. The mobile device configured to customize the configuration of claim 14, wherein the two pairs of capacitive proximity sensors are arranged on the rear surface of the housing of the mobile device.

16. The mobile device configured to customize the configuration of claim 10, wherein the processor-readable instructions configured to cause the one or more processors to customize the configuration of the mobile device comprises processor-readable instructions configured to cause the one or more processors to select functions from a set of functions available to the user at least partially based on the hand size of the user.

17. The mobile device configured to customize the configuration of claim 10, wherein the processor-readable instructions further comprise processor-readable instructions configured to cause the one or more processors to:
- receive proximity data for each user of a plurality of users, wherein:
  - the plurality of users comprises the user; and
  - the proximity data corresponding to each user is used to determine the hand size for each user of the plurality of users; and
- cause a user profile for each user to be stored, wherein the user profile identifies the hand size for the corresponding user.

18. A computer program product residing on a non-transitory processor-readable medium for customizing a configuration of a mobile device, the computer program product comprising processor-readable instructions configured to cause one or more processors to:
- receive proximity data;
- determine that a user has gripped the mobile device based on the proximity data;
- determine a hand size of the user using the proximity data;
- determine whether the user is an adult or a child based on the hand size; and
- customize the configuration of the mobile device at least partially based on whether the user is the adult or the child.

19. The computer program product of claim 18, wherein the processor-readable instructions configured to cause the one or more processors to customize the configuration of the mobile device further comprises processor-readable instructions configured to cause the one or more processors to limit a data transmission rate of the mobile device.

20. The computer program product of claim 18, wherein the computer program product further comprises processor-readable instructions configured to cause the one or more processors to:
- cause a text message routed to the mobile device at least partially based on the user gripping the mobile device to be presented, wherein a mobile phone linked with the user does not ring or vibrate in response to the text message.

21. The computer program product of claim 18, wherein the processor-readable instructions configured to cause the one or more processors to determine that a user has gripped the mobile device based on the proximity data further comprises processor-readable instructions configured to cause the one or more processors to, using the proximity data, determine that the user has gripped the mobile device with two hands.

22. The computer program product of claim 21, wherein the processor-readable instructions configured to cause the one or more processors to determine the hand size of the user using the proximity data further comprises processor-readable instructions configured to cause the one or more processors to:
- determine a first hand size of a left hand of the user and a second hand size of a right hand of the user.

23. The computer program product of claim 18, wherein the processor-readable instructions configured to cause the one or more processors to customize the configuration of the mobile device further comprises processor-readable instructions to cause the one or more processors to select functions from a set of functions available to the user at least partially based on the hand size of the user.

24. The computer program product of claim 18, wherein the computer program product further comprises processor-readable instructions configured to cause the one or more processors to:
- receive proximity data for each user of a plurality of users, wherein:
  - the plurality of users comprises the user; and
  - the proximity data corresponding to each user is used to determine the hand size for each user of the plurality of users; and
- cause a user profile for each user to be stored, wherein the user profile identifies the hand size for the corresponding user.

25. An apparatus for customizing a configuration of a mobile device, the apparatus comprising:
- means for collecting proximity data;
- means for determining that a user has gripped the mobile device based on the proximity data;
- means for determining a hand size of the user using the proximity data;
- means for determining whether the user is an adult or a child based on the hand size; and
- means for customizing the configuration of the mobile device at least partially based on whether the user is the adult or the child.

26. The apparatus for customizing the configuration of the mobile device of claim 25, wherein the means for customizing the configuration of the mobile device comprises:
- means for limiting a data transmission rate of the mobile device.

27. The apparatus for customizing the configuration of the mobile device of claim 25, further comprising:
- means for presenting a text message routed to the mobile device at least partially based on the user gripping the mobile device, wherein a mobile phone linked with the user does not ring or vibrate in response to the text message.

28. The apparatus for customizing the configuration of the mobile device of claim 25, wherein the means for determining that a user has gripped the mobile device based on the proximity data comprises:
- means for determining, using the proximity data, that the user has gripped the mobile device with two hands.

29. The apparatus for customizing the configuration of the mobile device of claim 25, wherein the means for determining the hand size of the user using the proximity data comprises:
- means for determining a first hand size of a left hand of the user and a second hand size of a right hand of the user.

30. The apparatus for customizing the configuration of the mobile device of claim 25, wherein:
- the means for customizing the configuration of the mobile device comprises means for selecting functions from a set of functions available to the user at least partially based on the hand size of the user.

* * * * *